US006149945A

United States Patent [19]
Mirzayans et al.

[11] Patent Number: 6,149,945
[45] Date of Patent: Nov. 21, 2000

[54] HUMAN FIBROBLAST DIFFUSABLE FACTORS

[75] Inventors: Razmik Mirzayans, Edmonton, Canada; Malcolm C. Paterson, Riyadh, Saudi Arabia

[73] Assignee: Alberta Cancer Board, Edmonton, Canada

[21] Appl. No.: 08/910,544

[22] Filed: Jul. 23, 1997

Related U.S. Application Data

[63] Continuation-in-part of application No. 08/407,883, Mar. 20, 1995, abandoned.

[51] Int. Cl.[7] .............................. A61K 35/12; C12N 13/00
[52] U.S. Cl. ......................................... 424/520; 435/173.1
[58] Field of Search ..................................... 530/350, 300, 530/324; 424/520; 435/173.1

[56] References Cited

U.S. PATENT DOCUMENTS

| | | | |
|---|---|---|---|
| 4,946,778 | 8/1990 | Ladner et al. | 435/69.6 |
| 5,424,400 | 6/1995 | Smith | 530/350 |

OTHER PUBLICATIONS

Coffman et al. "Control of DNA replication in a transformed lymphoid cell line: Coexistence of activator and inhibitor activities" Cellu. Immunol. 138, 381–389, 1991.
El–Deiry et al. "WAF1, a potential mediator of p53 tumor suppression" Cell 75, 817–825, 1993.
Waga et al. "The p21 inhibitor of cyclin–dependent kinases control DNA replication by interaction with PCNA" Nature 369, 574–578, Jun. 1994.
Akagi et al., 1987, "Mitogenic and Antimitogenic Transforming Growth Factors Secreted by Adenovirus 2– and Simian Virus 40–transformed Hamster Cells: Possible Roles in Promoting Tumorigenesis," Cancer Res. 47:4086–4092.
Aurias and Dutrillaux, 1986, "A possible new type of chromosome rearrangement: telomere–centromere translocation (tct) followed by double duplication," Hum. Genet. 72:25–26.
Aurias and Dutrillaux, 1986, "Probable involvement of immunoglobulin superfamily genes in most recurrent chromosomal rearrangements from ataxia telangiectasia," Hum. Genet. 72:210–214.
Bar et al., 1978, "Extreme Insulin Resistance in Ataxia Telangiectasia: Defect in Affinity of Insulin Receptors," New Eng. J. Med. 298:1164–1171.
Bigbee et al., 1989, "Evidence for an Elevated Frequency of In Vivo Somatic Cell Mutations in Ataxia Telangiectasia," Am. J. Hum. Genet. 44:402–408.
Carter et al., 1992, "Humanization of an anti–p185[HER2] antibody for human cancer therapy," Proc. Natl. Acad. Sci. U.S.A. 89:4285–4289.
Coffin, J., In: RNA Tumor Viruses, Weiss, R. et al. (eds.), Cold Spring Harbor Laboratory, vol. 2, pp. 36–38 (1985).
Cole et al., 1985, "The EBV–Hybridoma Technique and Its Application to Human Lung Cancer," Monoclonal Antibodies and Cancer Therapy, Alan R. Liss, Inc., pp. 77–96.

Croce et al., 1985, "Gene for α–Chain of Human T–Cell Receptor: Location on Chromosome 14 Region Involved in T–Cell Neoplasms," Science 227:1044–1047.
Gatti et al., 1991, "Ataxia–Telangiectasia: An Interdisciplinary Approach to Pathogenesis," Medicine 70:99–117.
Hartwell, 1992, "Defects in a Cell Cycle Checkpoint May Be Responsible for the Genomic Instability of Cancer Cells," Cell 71:543–546.
Hartwell and Weinert, 1989, "Checkpoints: Controls That Ensure the Order of Cell Cycle Events," Science 246:629–634.
Henderson et al., 1985, "Diagnosis of Ataxia–Telangiectasia by T–Lymphocyte Cloning Assay," Lancet 11:1242.
Hernandez et al., 1993, "A family showing no evidence of linkage between the ataxia telangiectasia gene and chromosome 11q22–23," J. Med. Genet. 30:135–140.
Huse et al., 1989, "Generation of a Large Combinatorial Library of the Immunoglobulin Repertoire in Phage Lambda," Science 246:1275–1281.
Jaspers and Bootsma, 1982, "Abnormal levels of UV–induced unscheduled DNA synthesis in ataxia telangiectasia cells after exposure to ionizing radiation," Mutat. Res. 92:439–446.
Jaspers et al., 1988, "Genetic complementation analysis of ataxia telangiectasia and Nijmegen breakage syndrome: a survey of 50 patients," Cytogenet. Cell Genet. 49:259–263.
Jones et al., 1986, "Replacing the complementarity–determining regions in a human antibody with those from a mouse," Nature 321:522–525.
Kastan et al., 1992, "A Mammalian Cell Cycle Checkpoint Pathway Utilizing p53 and GADD45 Is Defective in Ataxia–Telangiectasia," Cell 71:587–597.
Kastan et al., 1991, "Participation of p53 Protein in the Cellular Response to DNA Damage," Cancer Res. 51:6304–6311.
Khanna & Lavin, 1993, "Ionizing radiation and UV induction of p53 protein by different pathways in ataxia–telangiectasia cells," Oncogene 8:3307–3312.
Kohler and Milstein, 1975, "Continuous cultures of fused cells secreting antibody of predefined specificity," Nature 256:495–497.
Kosbor and Roder, 1983, "The production of monoclonal antibodies from human lymphocytes," Immunology Today 4:72–79.

(List continued on next page.)

Primary Examiner—Nashaat T. Nashed
Attorney, Agent, or Firm—Pennie & Edmonds LLP

[57] ABSTRACT

The present invention provides for numerous cell factors involved in a novel cellular pathway that is activated in response to ionizing radiation. Several cell factor activities are described which either complement the radioresistant DNA synthesis phenotype of Ataxia Telangiectasia cells, or inhibit DNA synthesis in the cell. Other cell factor activities are described which inhibit mitosis by arresting the cell cycle prior to cell division. It is contemplated that compositions comprising the subject factors will be useful as both research tools, and as therapeutic agents.

35 Claims, 8 Drawing Sheets

OTHER PUBLICATIONS

Kuerbitz et al., 1992, "Wild–type p53 is a cell cycle checkpoint determinant following irradiation," *Proc. Natl. Acad. Sci. U.S.A.* 89:7491–7495.

Kuhnlein and Paterson, 1990, "Increased uracil–DNA glycosylase, AP–DNA binding protein and deoxyribonuclease activities in tumor and SV40–transformed cell lines of human origin," *Carcinogenesis* 11:117–121.

Lehmann et al., 1979, "Abnormal Kinetics of DNA Synthesis in Ultraviolet Light–irradiated Cells from Patients with Cockayne's Syndrome," *Cancer Res.* 39:4237–4241.

Mirzayans and Paterson, 1991, "Lack of correlation between hypersensitivity to cell killing and impaired inhibition of DNA synthesis in ataxia telangiectasia fibroblasts treated with 4–nitroquinoline 1–oxide," *Carcinogenesis* 12:19–24.

Mohamed et al., 1987, "A Defect in DNA Topoisomerase II Activity in Ataxia–Telangiectasia Cells," *Biochem. Biophys. Res. Commun.* 149:233–238.

Morrison et al., 1984, "Chimeric human antibody molecules: Mouse antigen–binding domains with human constant region domains," *Proc. Natl. Acad. Sci. U.S.A.* 81:6851–6855.

Mulligan, R.C., Chapter 8, In: *Experimental Manipulation of Gene Expression*, Academic Press, pp. 155–173 (1983).

Murnane and Painter, 1982, "Complementation of the defects in DNA synthesis in irradiated and unirradiated ataxia–telangiectasia cells," *Proc. Natl. Acad. Sci. U.S.A.* 79:1960–1963.

Neuberger et al., 1984, "Recombinant antibodies possessing novel effector functions," *Nature* 312:604–608.

Painter and Young, 1980, "Radiosensitivity in ataxia–telangiectasia: A new explanation," *Proc. Natl. Acad. Sci. U.S.A.* 77:7315–7317.

Pippard et al., 1988, "Cancer in Homozygotes and Heterozygotes of Ataxia–Telangiectasia and Xeroderma Pigmentosum in Britain," *Cancer Res.* 48:2929–2932.

Reichmann et al., 1988, "Reshaping human antibodies for therapy," *Nature* 332:323–327.

Rosin and Ochs, 1989, "Heterogeneity of chromosomal breakage levels in epithelial tissue of ataxia–telangiectasia homozygotes and heterozygotes," *Hum. Genet.* 83:133–138.

Rosin and Ochs, 1986, "In vivo chromosomal instability in ataxia–telangiectasia homozygotes and heterozygotes," *Hum. Genet.* 74:335–340.

Russo et al., 1989, "Molecular analysis of a t(14;14) translocation in leukemic T–cells of an ataxia telangiectasia patient," *Proc. Natl. Acad. Sci. U.S.A* 86:602–606.

*Eng. J. Med. 300*:700–704.

Shaham and Becker, 1981, "The Ataxia Telangiectasia Clastogenic Factor is a Low Molecular Weight Peptide," *Hum. Genet.* 58:422–424.

Shiloh et al., 1989, "$G_2$ chromosomal radiosensitivity in families with ataxia–telangiectasia," *Hum. Genet.* 84:15–18.

Swift et al., 1991, "Incidence of Cancer in 161 Families Affected by Ataxia–Telangiectasia," *New Eng. J. Med.* 325:1831–1836.

Swift et al., 1987, "Breast and Other Cancers in Families with Ataxia–Telangiectasia," *New Eng. J. Med.* 316:1289–1294.

Takeda et al., 1985, "Construction of chimaeric processed immunoglobulin genes containing mouse variable and human constant region sequences," *Nature* 314:452–454.

Verhoeyen et al., 1988, "Reshaping Human Antibodies: Grafting an Antilysozyme Activity," *Science* 239:1534–1536.

Woods and Taylor, 1992, "Ataxia Telangiectasia in the British Isles: The Clinical and Laboratory Features of 70 Affected Individuals," *Quart. J. Med.* 82:169–179.

Wooster et al., 1993, "Absence of linkage to the ataxia telangiectasia locus in familial breast cancer," *Hum. Genet.* 92:91–94.

HUMAN FIBROBLAST DIFFUSABLE FACTORS

This is a continuation in part of U.S. application Ser. No. 08/407,883, filed Mar. 20, 1995, now abandoned which is herein incorporated by reference.

1.0. INTRODUCTION

The present invention relates to mammalian cell biology, and discloses novel biochemical factors elaborated by mammalian fibroblasts. At least one of these factors is a novel protein which is capable of directing the temporary and reversible arrest of DNA synthesis in normal mammalian cells. Another novel factor of the subject invention relates to the reversible arrest of the cell cycle prior to mitosis. Hence, it is contemplated that the subject factors will be useful as research tools for studying cell growth, intracellular signal transduction, and as therapeutics for reducing the radio-sensitivity of Ataxia Telangiectasia patients and carriers.

2.0. BACKGROUND

The normal eucaryotic cell cycle typically comprises four main stages: the $G_1$, S, $G_2$, and M phases. The replication of DNA and the production of histones occur during the S phase. This period of DNA synthesis is flanked by two "gap" periods, the $G_1$ and $G_2$ phases, during which pre- and post-replication DNA repair may occur, respectively, and during which the cell continues to produce the cellular macromolecules required for cell division. After the $G_2$ phase, the cell will enter the M phase, wherein the cell will divide by mitosis.

After irradiation, normal mammalian cells generally enter a period either where DNA synthesis is arrested, or where the cell is arrested in the $G_2$ phase. This period of arrest provides a "checkpoint" in the cell cycle which allows time for the repair of damaged/mismatched DNA templates, and prevents the segregation of damaged chromosomes. Irradiation induced inhibition of DNA synthesis has been the subject of intensive research for many years (Hartwell and Weinert, 1989, Science). Recent results have reported a direct link between the ability of human cells to arrest in $G_1$ phase following irradiation, and the status of the p53 tumor suppressor gene (Kasten et al., 1991 *Cancer Res.* 51:6304–6311; Kuerbitz et al., 1992, *Pro. Natl. Acad. Sci. USA* 89:7491–7495). In brief, these studies linked irradiation with increased levels of p53 protein. Further studies have demonstrated that inhibitors of protein kinase C (PKC) may prevent enhanced p53 expression after irradiation (Khanna & Lavin, 1993 *Oncogene* 8:3307–3312). These data cumulatively suggest that both PKC and p53 may play a role in irradiation induced inhibition of DNA synthesis.

2.1. Ataxia Telanqiectasia

Ataxia telangiectasia (AT) is an autosomal recessive, multisystem disorder characterized by progressive neuromuscular and vascular degeneration. AT is transmitted at an estimated frequency of one per 10,000 live births. AT patients exhibit cerebellar ataxia; oculocutaneous telangiectases; and various immune defects including hypoplasia of the thymus and sinopulmonary infections. Chromosomal breakage and rearrangement are common in AT cells, which are abnormally sensitive to ionizing radiation. Thus, both AT patients and carriers are predisposed to malignancy.

Onset of AT generally occurs by 3 years of age, and the first symptom is usually truncal ataxia (Woods, C. G. and Taylor, A. M. R. (1992) Quart. J. Med. 82:169–179). Truncal ataxia, which precedes appendicular ataxia, is characterized by deep tendon reflexes which become diminished or absent by age 8. Over time, patients lose large-fiber sensation. By their twenties and early thirties, many AT patients develop progressive spinal muscular atrophy which mostly affects the hands and feet. Familial studies revealed that idiopathic scoliosis and vertebral anomalies occurred in excess in the relatives of AT patients.

Ataxia was reviewed, inter alia, in *The Merck Manual of Diagnosis and Therapy*, 16th Ed. (1992) Merck Research Laboratories, Rahway, N.J.

2.2. AT-Associated Chromosomal Correlations

The basic defect associated with AT is thought to involve one or more of the enzymes concerned with DNA repair or processing. Although no major gene candidates have been identified, Kuhnlein and Paterson (1990, Carcinogenesis 11:117–121) reported a 5–6 fold increase in activity for uracil DNA glycosylase and DNAse III/IV and a 2–3 fold increase in apurinic/apyrimidinic DNA-binding protein. A tight chromosomal linkage is found between AT and THY1, a glycoprotein which is a major cell surface constituent of thymocytes and neurons. In addition, genes of the immunoglobulin superfamily, including CD3 and NCAM, are located near the AT region of chromosome 11.

Aurias and Dutrillaux (1986a, Hum. Genet. 72:25–26; 1986b, Hum. Genet. 72:210–214) reported that AT patients tend to have a high frequency of chromosomal breakage, not involving the AT locus itself, which leads to both translocations and inversions. The sites of breakage and rearrangements mostly involve those regions of chromosomes 2, 7, 14, and 22 where the immunoglobulin genes (IgK, IgH, and IgL) and the T-cell receptor genes (TCR-α, -β, and -γ) are located. Ig clusters are known hot spots for breakage and rearrangements and are associated with several diseases. Previously, Croce et al. (1985, Science 227:1044–1047) had suggested that the oncogene TCL1, which is located in the region of the chromosome 14 breakpoint, may be activated by chromosome inversion or translocation, perhaps in juxtaposition with the TCR-α gene. Russo et al. (1989, Proc. Natl. Acad. Sci. 86: 602–606) presented further evidence of a cluster of breakpoints in the region of the putative oncogene TCL1 in AT patients with chronic lymphocytic leukemia.

Shaham and Becker (1981, Hum. Genet. 58:422–424) identified an AT clastogenic (chromosome breaking) factor in the plasma of AT patients and in the culture medium of AT skin fibroblasts. This small peptide has a molecular weight in the range of 500 to 1000. Although clastogenic activity could not be demonstrated using cell extracts, cultured AT fibroblasts are reported to show spontaneous chromosomal recombination rates 30 to 200 times higher than found in cultured normal fibroblasts. Hence, these increased recombinations, translocations and other chromosomal aberrations in lymphocytes, monocytes and fibroblasts undoubtedly contribute to increased cancer risk.

Abnormal V(D)J recombination, joining V segments of the TCR-gamma with J segments of TCR-β occurs in peripheral blood lymphocytes of AT patients at a frequency 50- to 100-fold higher than normal. This frequency is roughly the same as the increase in the risk for lymphoid malignancy in these individuals. In addition, the J-α sequence has been implicated in some T-cell translocations which remove chromosomal material between q12 and q32 of chromosome 11 (Russo et al. (1989) Proc. Natl. Acad. Sci. 86: 602–606).

All of these examples strongly imply that the immunodeficiencies associated with AT are due to the physical loss or functional inactivation of genetic material. This hypothesis is further substantiated by the fact that AT homozygotes commonly display a 5- to 14-fold increase in the frequency of oral exfoliated cell micronuclei. In AT, this easily scorable cytogenetic abnormality can be used as a diagnostic tool to identify AT heterozygotes who commonly display an intermediate frequency of such micronuclei (Rosin et al., 1989 Hum. Genet. 83:133–138).

Bigbee et al. (1989, Am. J. Hum. Genet. 44:402–408) demonstrated an increased frequency of somatic cell mutation in vivo in individuals with AT. The authors speculated that the predisposition to somatic cell mutation may be related to the increased susceptibility to cancer in AT homozygotes. Heterozygotes for the disease did not appear to have a significantly increased frequency of such mutations.

2.3. AT-Associated Sensitivity to Radiation/Cell Cycle

The AT region seems to be involved in a signal transduction pathway that controls cell cycle arrest following DNA damage. The AT region is upstream of the p53 gene, which theoretically plays a role in the $G_1$-S checkpoint, which delays the cell cycle of cells with damaged DNA. In normal cells, p53 levels increase 3- to 5-fold by a post-transcriptional mechanism after γ-irradiation; however, augmented p53 expression, and its subsequent induction of GADD45, does not occur in irradiated AT cells (Kastan et al. (1992) Cell 71:587–597). Another feature of AT cells is that they do not temporarily arrest DNA synthesis in response to irradiation. Thus, radioresistant DNA synthesis is a diagnostic feature of AT cells.

In fact, checkpoints at both the $G_1$-S and the $G_2$-M transitions (Hartwell (1992) Cell 71:543–546) allow the cell to delay progression through the cell cycle. Checkpoints are thought to serve as surveillance mechanisms which detect DNA damage, and initiate the proper signal transduction pathways required to initiate appropriate DNA repair mechanisms.

Painter and Young (1982 Proc. Natl. Acad. Sci. 77:7315–7317) showed that the $G_1$-S checkpoint does not function in cells from AT patients. If the DNA is not repaired, abnormalities which could contribute to tumor development become permanent during the S phase. In fact, lymphoid, breast and other cancers are known to be increased in individuals heterozygous for germ line mutations of either p53 or the AT gene (Swift et al. 1991 New Eng. J. Med. 325:1831–1836; 1987, New Eng. J. Med. 316:1289–1294).

In addition to loss of function at the $G_1$-S checkpoint, Shiloh et al. (1989, Hum. Genet. 84:15–18) presented evidence that the extent of chromatid damage induced in the $G_2$ phase of the cell cycle by a moderate dosage of x-rays is markedly higher in AT cells than in normal cell controls. These data correlate with the inability of some AT cells to carry out DNA synthesis during the S phase of the cell cycle (Mohamed et al. (1987) Biochem. Biophys. Res. Commun. 149:233–238). Because patients with AT are unusually sensitive to x-rays, treatment of malignancy with conventional dosages of radiation can be fatal to them.

2.4. AT-Associated Biochemistry

AT patients usually show an increase in serum alpha-fetoprotein. This is consistent with immature development of the liver and suggests that tissue differentiation is a primary AT defect. Patients also show a decrease in immunoglobulins, although different patients may show different immunoglobulin (Ig)-A, -E, and -G2 levels, ranging from normal to completely absent. DNA topoisomerases I and II, enzymes that introduce transient single- and double-strand breaks, are also expressed at abnormal levels in some, but not all, AT cell lines. These variations appear to be correlated with various chromosomal rearrangements as discussed below.

In contrast, the severity of sinopulmonary infections such as staphylococcal pneumonia, chronic bronchitis, etc., do not necessarily correlate with AT-associated immunodeficiency and may be related to other genetic factors.

Furthermore, endocrine abnormalities such as gonadal dysgenesis or atrophy and an unusual form of diabetes mellitus in which glucose tolerance is markedly decreased have been reported. Experiments examining insulin resistance suggest the presence of antireceptor immunoglobulins in the plasma of AT patients (Bar et al. (1978) New Eng. J. Med. 298:1164–1171). Mental retardation is also sometimes associated with AT, and some older patients may suffer a severe loss of short-term memory (Gatti et al. (1991) Medicine 70:99–117).

2.5. AT-Associated Malignancy

Patients with AT have a strong predisposition to malignancy, and in particular to lymphomas and chronic lymphatic leukemia. About one-third of patients develop malignancies during their shortened, less than 50 year, life-span. In general, lymphomas in AT patients tend to be of B-cell origin, whereas leukemias tend to be of the T-cell type. Furthermore, neoplastic cells are often of thymic origin. In addition, Saxon et al. (1979, New Eng. J. Med. 300:700–704) have suggested that malignant transformation of uncommitted T-lymphocyte precursors capable of differentiation contribute to the chronic lymphatic leukemia often reported for AT patients. Solid tumors, including medulloblastomas and gliomas, occur at elevated rates in AT patients (Gatti et al. (1991) Medicine 70:99–117).

Heterozygotes, who are also said to be predisposed to lymphomas, have a relative risk of developing cancer compared to the normal population of about 3.7 (Swift et al. (1991) New Eng. J. Med. 325:1831–1836). Using documented cancer incidence (rather than cancer mortality) in persons heterozygous for AT, relative risk of cancer of all types was 3.8 for men and 3.5 for women. The relative risk for breast cancer, the cancer most clearly associated with AT, in carrier women was 5.1. In two independent studies, 8 to 18 percent of patients with breast cancer were confirmed to be AT heterozygotes (Swift et al. (1987) New Eng. J. Med. 316:1289–1294; Pippard et al. (1988) Cancer Res. 48:2929–2932). Since the genes responsible for most cases of AT are located on chromosome 11q, Wooster et al. (1993, Hum. Genet. 92:91–94) typed 5 DNA markers in the AT region in 16 breast cancer families. They found no evidence for linkage between familial breast cancer and these markers and concluded that the contribution of AT to familial breast cancer is likely to be minimal.

2.6. Genetic Complementation

As early as 1977, Paterson et al. (*Research in Photobiology*, Plenum, New York) suggested the existence of two distinct types of ataxia telangiectasia. By 1988, Jaspers et al. (Cytogenet. Cell Genet. 49:259–263) had used genetic complementation studies on fibroblasts to identify six different genetic complementation groups. Four of these, called AB, C, D, and E, are clinically indistinguishable, present no group-specific patterns of clinical characteristics or ethnic origin, and display frequencies among AT patients of approximately 55%, 28%, 14%, and 3%, respectively. Hernandez et al. (1993, J. Med. Genet. 30:135–140) cited evidence for the existence of these four complementation groups: AB, C, D, and E on chromosome 11q. Interestingly, the group D defect was corrected by transfer of genetic material from chromosomal region 11q22-q23 into an AT affected fibroblast cell line, and group E cells have a deoxyribophosphodiesterase deficiency.

2.7 Beta Integrins

The integrin family comprises 14 alpha subunits and 8 beta subunits (Hynes (1992) Cell 69:11–25). A functional structure consists of one alpha and one beta subunit which partially extrudes from the cell. The receptor is a dimer which connects the cytoskeleton with the extracellular matrix proteins.

One of the primary roles of the integrins is cell adhesion. In their connection with the proteins of the extracellular matrix, integrins are in close proximity to growth factors and they act as anchors for individual cells such as platelets and lymphocytes. Internally, they interact with talin molecules of the cytoskeleton and provide a more stable structural framework for tissues such as the skin, organs such as the liver, and the arteries and veins of the vascular system.

In their transmembrane role, the alpha and beta integrins appear to be bidirectional signaling proteins. They are among a select few molecules that propagate messages from the inside of the cell to the outside. Signaling function is explained or modeled via conformational changes. Specifically, this occurs by interaction between the alpha and beta integrin subunits, which are associated with the signal transduction pathway. As signal receptors, these molecules regulate intracellular pH, intracellular free calcium, tyrosine phosphorylation of proteins and inositol lipid turnover.

Slight alterations, even point mutations, can be correlated with the loss of signaling. Lack of appropriate integrin signaling may be associated with the failure to halt the cell cycle for repair of chromosomal damage following chemical or physical disruption (such as ionizing radiation) and result in the higher cancer incidence seen in AT patients and carriers.

Integrins play a role in the immune response through activation of lymphocytes and the maturation of B-cells. It also appears that integrins may be downregulated or absent in AT cells. The relative dearth of integrins could explain the structural and functional immaturity of the liver and some of the immune and metastatic complications which are often associated with AT. Finally, when the secretion of integrins is blocked, cells undergo apoptosis. This apoptosis could affect fetal development and result in the non-Mendelian ratios seen in the inheritance of AT. In particular, it appears that a deficiency of integrin beta subunit 1 characterizes the major genetic form of AT, namely complementation group AB.

2.8. Present Methods of At-Diagnosis

Early-onset ataxia with telangiectasia permits diagnosis of AT. Before the appearance of telangiectasia, clinical diagnosis is problematic because cerebellar ataxia and oculomotor apraxia are also typical of X-linked Pelizaeus-Merzbacher disease and Joubert's syndrome. Elevated levels of alpha-fetoprotein and carcinoembryonic antigen are the most useful clinical markers (Gatti et al. (1991) Medicine 70:99–117). Dysgammaglobulinemia, decreased cellular immune responses, and peripheral lymphopenia are supportive findings, but they may or may not be expressed in all AT patients.

Henderson et al. (1985, Lancet 11:1242) devised a rapid diagnostic method based on the hypersensitivity of AT lymphocytes to gamma irradiation. Similar studies have employed fibroblasts or chorionic villus sampling. Shiloh et al. (1989, Hum. Genet. 84:15–18) used the extent of X-ray damage to chromatids in the G2 phase of AT heterozygous cells as a test of heterozygosity.

Painter and Young (1980, Proc. Natl. Acad. Sci. 77:7315–7317), however, questioned the reliability of this approach on the basis that radiosensitivity of AT cells may be caused by their failure to delay DNA synthesis after radiation damage (See, §2.3. AT-Associated Sensitivity to Radiation/Cell Cycle above).

The exfoliated cell micronucleus test is performed on cells from either the oral cavity, collected by swabbing the mucosa, or the urinary bladder, obtained by centrifugation of fresh urine specimens. Micronuclei are membrane-bound, Feulgen-positive, acentric fragments which result from fragmentation of chromosomes during division of epithelial cells. Both AT homozygotes and heterozygotes can be identified by this method (Rosin and Ochs 1986, Hum. Genet. 74:335–340, 1989 Hum. Genet. 83:133–138).

2.9. Description of Fibroblasts

The fibroblast is the most common cell type in connective tissue. The term "fibroblast" is often used to describe cells which share similar morphology but carry out different functions. Fibroblasts include connective-tissue stem cells, matrix- and other protein-synthesizing cells, contractile cells, and phagocytic cells. Active fibroblasts are characterized by their abundant endoplasmic reticulum (ER), Golgi complex and ribosomes. Fibroblasts synthesize actin-myosin filaments, the matrix elements (collagen, reticular and elastic fibers), and glycosaminoglycans and glycoproteins, which are secreted as amorphous intercellular substance.

Fibroblasts play a particularly critical role during embryogenesis. Besides synthesizing proteins, they determine the structure of the skeleton, the location of muscle cells, the growth patterns of nerve fibers and the organization of the skin. Fibroblasts accomplish these organizational functions by attaching collagenous fibrils to embryonic cells and pulling them into the proper alignment to form parts of the developing organism.

During human development and throughout adulthood, fibroblasts continue to synthesize and maintain both loose and dense types of connective tissue. They migrate in response to a number of chemoattractants such as lymphokines, cytokines and growth factors and constantly remodel and repair tissues by producing various degradative and synthetic enzymes, including collagenase, and products that may modulate the function of other cells including prostaglandins, tissue plasminogen activator (tPA), complement components and superoxide dismutase. The importance of fibroblasts may be attributed to their production of collagen, the predominant extracellular component of connective tissue and the most abundant protein in the human body.

The biology of fibroblasts and matrix proteins is discussed by Postlethwaite and Kang, In: *Inflammation: Basic Principles and Clinical Correlates,* 2d ed, Gallin et al. (1992) Raven Press, New York, pp 747–773.

3.0. SUMMARY OF THE INVENTION

The subject invention provides for methods and processes for the production, biochemical purification, recombinant cloning and manipulation, over expression and use of numerous factors which are elaborated by normal mammalian cells after exposure to ionizing radiation.

As such, the present invention contemplates methods of using ionizing radiation to induce the expression of novel cellular factors which mediate novel cellular signaling cascades which substantially arrest DNA synthesis and cell progression through the cell cycle.

An additional embodiment of the claimed invention includes compositions comprising the protein factor products of the above process which are capable of substantially arresting or inhibiting DNA synthesis to substantially the same extent as at least about 40 Gy of ionizing irradiation.

The subject invention further contemplates compositions comprising DNA synthesis inhibiting factor (SIF), or factors (SIFs), capable of reversibly and, optionally, temporarily arresting or inhibiting DNA synthesis in mammalian cells. At least one of these factors, $G_1$-arresting factor, is capable of temporarily arresting DNA synthesis prior to the S phase. The subject invention also contemplates compositions comprising heat-stable factors which arrest the cell cycle at the $G_2$ phase, and thereby function as mitosis inhibiting factor (MIF) or factors (MIFs). At least one of these factors, the $G_2$-arresting factor ("$G_2AF$"), is capable of arresting the cell in the $G_2$ phase prior to entering the M phase. The claimed DNA synthesis inhibiting factors (SIFs) and the mitosis inhibiting factors (MIFs) are useful for treating and reducing the adverse medical consequences of irradiation which are suffered by radiosensitive AT patients and carriers.

The subject invention also contemplates compositions comprising a factor (e.g., DRFs, damage recognition factors), or factors, which are capable of directly mediating the inhibition of DNA synthesis. Furthermore, the subject invention contemplates compositions comprising a factor or factors which are capable of directly mediating cell division (CDFs).

Another embodiment of the present invention includes diffusible protein factors which are capable of complementing and correcting radioresistant DNA synthesis and cell division in AT cells. These AT-complementing factors may be produced by normal cells or by AT-cells of various complementation groups, and are also useful for treating and reducing the adverse medical consequences of irradiation which are suffered by radiosensitive AT patients and carriers.

An additional embodiment of the claimed invention is a novel composition comprising a protein activity useful for the production of substantially synchronous populations of mammalian cells.

4.0. DESCRIPTION OF THE FIGURES

FIG. 1 is a graph of the log of the percent of AT or normal cells surviving after being subject to 0, 2, 4, or 6 Gy of irradiation. AT cells (triangles and squares) or GM38 (normal fibroblasts, circles) were coincubated with either GM38 (solid triangles or circles), or AT (solid squares) feeder cells for 48 hours prior to irradiation. The percent of cells surviving irradiation was measured by colony forming ability.

FIGS. 2a–d show that the radioresistant DNA synthesis characteristic of AT cells may be complemented either by AT cells of a different complementation group, or by normal fibroblasts. FIGS. 2a–d show the amount of DNA synthesis, measured by in situ autoradiography, as a function of radiation dosage after AT group B (a), AT group A (b), AT group D (c), and GM38 (d) cells (normal fibroblasts) were coincubated with: GM38 normal fibroblasts (solid circles); group B AT cells (open triangles); group A AT cells (open circles); or group D AT cells (open diamonds).

FIG. 3 shows the DNA synthesis inhibiting activity of SIF factor. Varying concentrations of extract comprising SIF factor were added to approximately $10^5$ HeLa cells and the amount of DNA synthesis was measured by scintillation counting after two hours of exposure to SIF factor (solid circles). Residual SIF factor activity remained after SIF extract was boiled for 10 minutes (open circles).

Figure 7:
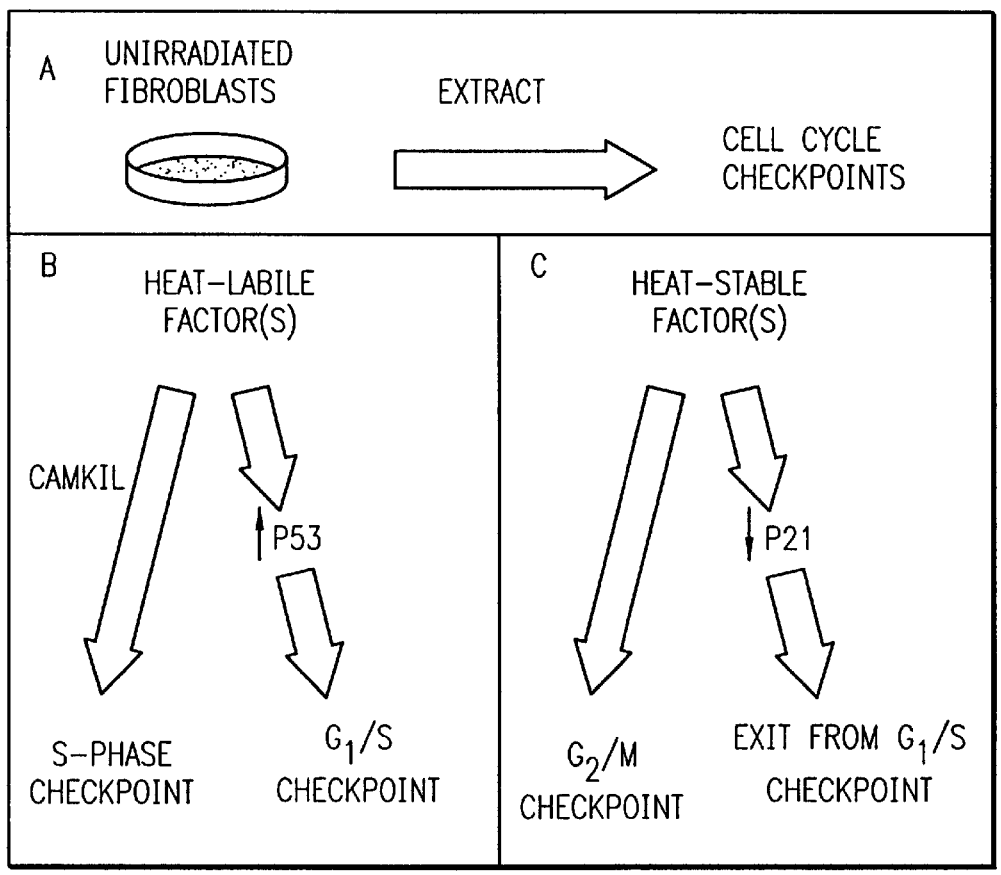

FIGS. 7a–c show schematics depicting the effects of whole cell extracts prepared from γ-irradiated HeLa cells on normal human fibroblast cultures (strain GM38). These effects are the same as those that occur following genotoxic stresses on the cells. FIG. 7a shows that the addition of γ-irradiated HeLa cell extract on normal human cells triggers activation of cell cycle checkpoints. FIG. 7b represents that one factor from the extract is a heat-labile factor which triggers the activation of two signalling pathways: (i) a pathway requiring calmodulin-dependant kinase II (CaMKII) which mediates inhibition of replicon initiation and DNA chain elongation processes (i.e. S-phase checkpoint), and (ii) a p53-dependant pathway which mediates G1/S checkpoint. FIG. 7c shows that another factor from the extract is a heat-stable factor that induces at least two responses: (i) inhibition of G2/M transition (G2/M checkpoint), and (ii) down-regulation of WAF1 (a p53-regulated gene whose product, p21, inhibits transition from G1 to S, coupled with release of cells from the previous G1/S checkpoint.

Figure 8:
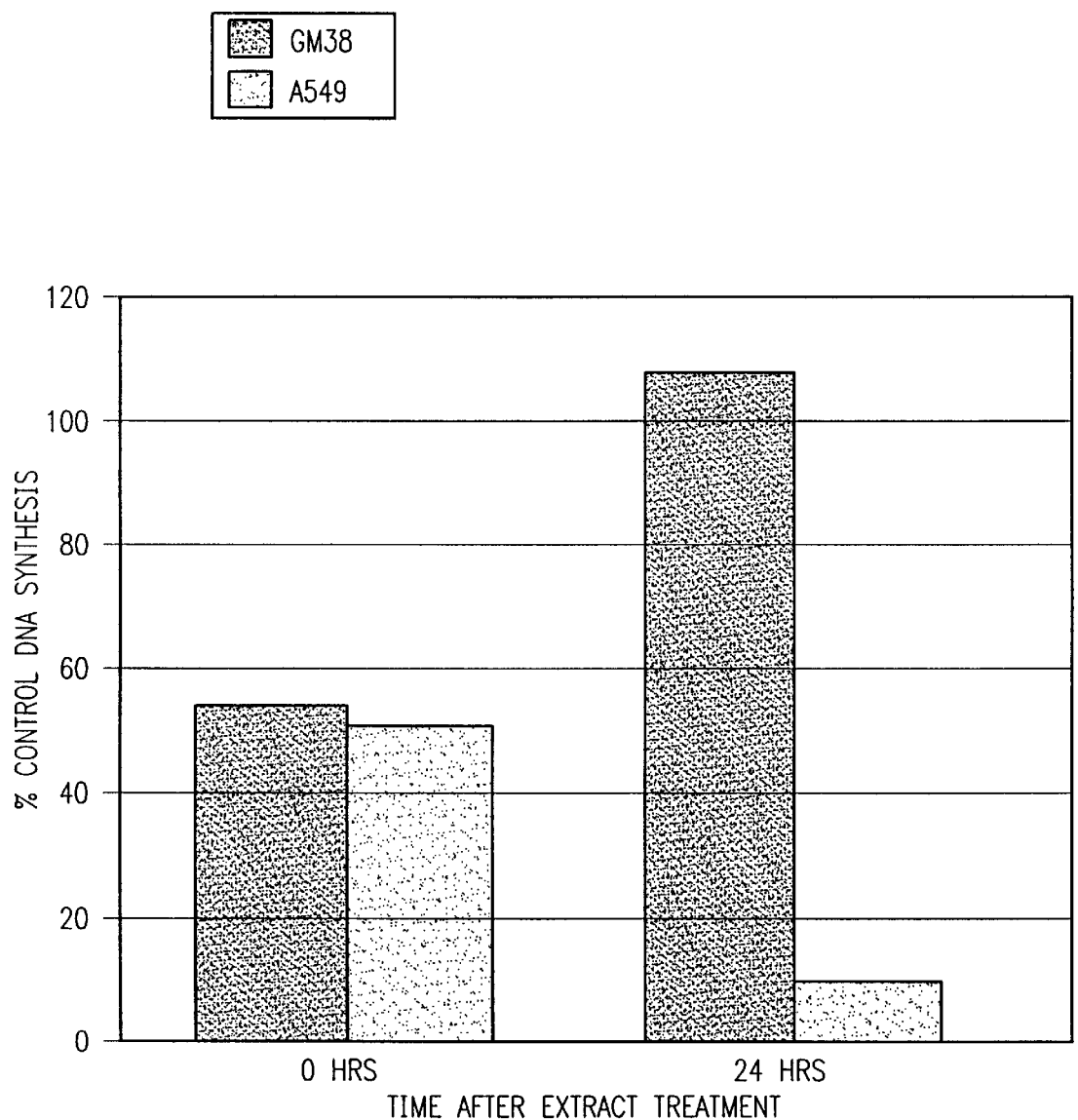

FIG. 8 shows differential responses of DNA synthesis of normal human fibroblasts (strain GM38) and human alveolar tumor cells (strain A549) to γ-irradiated HeLa cell extracts.

5.0. DETAILED DESCRIPTION OF THE INVENTION

The present invention provides numerous factors which are produced by normal mammalian cells after exposure to ionizing radiation. The subject factors may be stored intracellularly (or extracellularly in the extracellular matrix) and activated or released in response to irradiation, or, alternatively, the genes encoding the factors may be transcribed and otherwise expressed de novo after irradiation.

The novel DNA synthesis inhibiting and mitosis inhibiting activities of the present invention define a novel cellular signal transduction cascade that is triggered in response to chromosomal damage. Thus, one embodiment of the present invention includes novel compositions comprising at least one of the novel DNA synthesis inhibiting factors discussed herein. Another embodiment includes compositions comprising at least one of the novel mitosis inhibiting factors discussed herein.

For the purposes of this application, the term ionizing radiation shall mean all forms of radiation, including but not limited to $\alpha$, $\beta$, and $\gamma$ radiation and U.V. light, which are capable of directly or indirectly damaging the genetic material of a cell or virus. The term irradiation shall mean the exposure of a sample of interest to ionizing radiation, and the term radiosensitive shall refer to cells or individuals which display unusually adverse consequences after receiving moderate, or medically acceptable (i.e., nonlethal diagnostic or therapeutic doses) exposure to ionizing irradiation.

Also for the purposes of this application, the term substantially synchronous population of cells shall mean that generally at least about 50 percent more of the cells in a given cell population will be at or in the same stage of cell division at a given point of interest; preferably at least about 75 percent more of the cells in a given population are at or in the same stage of cell division; and optimally at least about 100 percent more of the cells in a given population will be at or in the same stage of cell division as compared to untreated control cells.

The terms substantially arresting or substantially inhibiting DNA synthesis or mitosis shall generally mean that the net level/amount of DNA synthesis or mitosis in treated cells shall be at least about 70 percent that of control or untreated cells, and preferably mean that the level of DNA synthesis or mitosis shall be about 50 percent that of control cells. Optionally, the extent of DNA synthesis or mitosis may be calculated on a per viable cell basis, and normalized accordingly.

The claimed factors may be exogenously added to cells in culture, or microinjected into individual cells. Following addition of the factors to the cells, the factors can be washed away or inhibited using antibodies. Hence, they can be made to reversibly inhibit DNA synthesis or induce $G_2$-phase arrest of the cells. The inhibition or the arrest caused by these factors may be relatively rapid, with inhibition of DNA synthesis being detectable in as little as 15 minutes after the factors are introduced to the target cells. As such, it is contemplated that the subject factors may be used to rapidly and substantially inhibit DNA synthesis of mammalian cells.

In addition to inhibiting DNA synthesis in normal cells, one or all of the DNA synthesis inhibiting factors (SIFs: characterized by inhibiting DNA synthesis via extracellular addition), damage recognition factors (DRFs: characterized by inhibiting DNA synthesis via intracellular introduction, e.g., microinjection), AT-complementing factors (ATCFs: characterized by their ability to inhibit radioresistant DNA synthesis in the suitable AT complementation group), or mitosis inhibiting factors (MIFs: characterized by their ability to arrest the cell at the $G_2$-phase) may be able to complement and correct the altered radioresistant DNA synthesis phenotype characteristic of AT cells. Since radioresistant DNA synthesis is an aberration that allows irradiated cells to reproduce and reassort DNA that has been damaged by irradiation, it is thought that such synthesis may play a role in the unusually high sensitivity to radiation that is characteristic of AT patients. By reducing radioresistant DNA synthesis, the present factors will find utility in reducing the radiosensitivity of AT patients. The ability to complement the radioresistant DNA synthesis phenotype of AT cells also provides the basis for a simple assay which may be used to test for AT complementing factor (ATCF) activity in fractions generated during purification studies.

Additionally, at least one of the SIFs ($G_1$-arresting factor) triggers a block in the cell cycle at or near the $G_1$-S phase transition. This $G_1$-blocking activity may prove particularly useful for substantially synchronizing the growth of eucaryotic cells. Furthermore, at least one of the MIFs ($G_2$-arresting factor) triggers a block in the cell cycle at or near the $G_2$-M phase transition.

The novel activities described as well as the AT complementation data cumulatively define a novel cellular signal cascade. In exerting an extracellular effect, SIFs and MIFs presumably represent endocrine, paracrine, or autocrine signals that interact with cellular receptors and trigger the cascade. The fact that various AT cells may be complemented by each other, or normal cells, indicates that the AT associated genetic lesions presumably effect the intermediary functions of the cellular cascade. Finally, by acting intracellularly, DRF is presumably produced or activated by the terminal portions of the cascade and is thought to represent the effector molecule, or molecules, which actually mediate the inhibition of DNA synthesis.

All of these factors affect cell-cycle checkpoints. One factor (SIF) is heat-labile and activates a calmodulin-dependent kinase II which mediates inhibition of replicon initiation and DNA chain elongation, and a p53-dependent pathway which mediates the $G_1$/S checkpoint. Another factor (MIF) is heat stable and induces inhibition of the $G_2$/M transition, and inhibits p21, which inhibits transition from $G_1$ to the S phase.

One unit of SIF activity shall be defined as that amount of SIF which is required to arrest or inhibit the DNA synthesis of approximately $10^2$ target cells to an extent that, at least about two hours after initial treatment, net DNA synthesis per viable target cell is at least about 60 percent that of untreated cells.

One unit of MIF activity shall be defined as that amount of MIF which is required to arrest or inhibit mitosis of approximately $10^2$ target cells to an extent that, at least about two hours after initial treatment, net mitosis per viable target cell is at least about 60 percent that of untreated cells.

One unit of AT-complementing factor (ATCF) activity shall be defined as that amount of factor which is required to arrest or inhibit radioresistant DNA synthesis of $10^2$ AT cells to an extent that the normalized (relative to normal cells) level of radioresistant DNA synthesis is reduced by at least about 25 percent.

One unit of DRF factor activity shall be defined as the amount of DRF factor required to inhibit DNA synthesis in target cells to an extent that DNA synthesis is reduced by at least about 20 percent (relative to control cells) at least 30 minutes after treatment.

Given the association between many forms of malignancy and either the heterozygous or homozygous presence of the AT gene, the claimed factors will also be useful for the prevention (by prophylactic treatment) of many forms of human cancer in AT patients and carriers.

To the extent that many cancer therapies (e.g., chemotherapy and radiation therapy) are designed to target replicating cells, clinicians would find it advantageous to target a synchronously replicating population of tumor cells. By targeting a synchronous population of tumor cells, a clinician could attack the tumor cells while an enhanced proportion of the cells are at or near a point in the cell cycle where they are maximally susceptible to the anti-tumor agent or procedure (i.e., irradiation and the like). Alternatively, the dosage of anti-tumor agent or procedure can be maximized at or near a point in the cell cycle where the tumor cells are most sensitive to treatment. Thus, an additional embodiment of the claimed factors is their use to substantially stall replication of a tumor cell population at or near a given point in the cell cycle whereby a substantially synchronous population of tumor cells is produced.

Alternatively, to the extent that tumor cells may be more or less sensitive to SIFs than normal cells in vivo, SIFs may be used to selectively inhibit DNA synthesis in normal cells or tissues (thus offering a level of protection from cancer therapeutic agents) while the clinician targets the replicating tumor cells. In fact, we have recently demonstrated that tumor cells maintain inhibition of DNA synthesis after SIF treatment longer than normal human fibroblasts.

Given that at least one subset of the subject irradiation-induced factors blocks mitosis(MIFs), an additional embodiment involves the use of the subject factors to block cell replication. By blocking cell replication, the subject factors may find use in the medical treatment of a variety of proliferative disorders (in addition to cancer) of the body including but not limited to psoriasis, auto-immune disease, fibrotic diseases, and the like.

Thus, an additional embodiment of the subject invention is the therapeutic use of a composition comprising human ATCFs, SIFs, MIFs, or derivatives thereof, as bioactive agents for the treatment or prevention of diseases including but not limited to Ataxia telangiectasia, autoimmune disorders and diseases, inflammation, cancer, graft rejection, and any of a variety of proliferative disorders.

One of ordinary skill will appreciate that, from a medical practitioner's or patient's perspective, virtually any alleviation or prevention of an undesirable symptom (e.g., symptoms related to disease, sensitivity to environmental or factors, normal aging, and the like) would be desirable. Thus, for the purposes of this Application, the terms "treatment", "therapeutic use", or "medicinal use" used herein shall refer to any and all uses of the claimed compositions which remedy a disease state or symptoms, or otherwise prevent, hinder, retard, or reverse the progression of disease or other undesirable symptoms in any way whatsoever.

When used in the therapeutic treatment of disease, an appropriate dosage of ATCF, MIF, MIF-ligand, SIF, SIF-ligand, or derivatives thereof, may be determined by any of several well established methodologies. For instance, animal studies are commonly used to determine the maximal tolerable dose, or MTD, of bioactive agent per kilogram weight. In general, at least one of the animal species tested is mammalian. Those skilled in the art regularly extrapolate doses for efficacy and avoiding toxicity to other species, including human. Before human studies of efficacy are undertaken, Phase I clinical studies in normal subjects help establish safe doses.

Additionally, the bioactive agent may be complexed with a variety of well established compounds or structures that, for instance, enhance the stability of the bioactive agent, or otherwise enhance its pharmacological properties (e.g., increase in vivo half-life, reduce toxicity, etc.).

Where diagnostic, therapeutic or medicinal use of ATCFs, MIFs, MIF-ligands, SIFs, SIF-ligands, or derivatives thereof, is contemplated, the bioactive agent may be introduced in vivo by any of a number of established methods. For instance, the agent may be administered by inhalation; by subcutaneous (sub-q); intravenous (I.V.), intraperitoneal (I.P.), or intramuscular (I.M.) injection; or as a topically applied agent (transdermal patch, ointments, creams, salves, eye drops, and the like).

Another embodiment of the subject invention involves the use of gene therapy to treat an AT carrier or AT afflicted individual by the administration and expression of nucleotides and/or polynucleotides encoding ATCFs, DRFs, MIFs, MIF-derivatives, SIFs, SIF-derivatives, or ligands thereof to the individual. Such gene therapy is intended to compensate for genetic deficiencies in the AT carrier's or AT afflicted individual's genome and may be effected by somatic cell gene therapy whereby host cells are transduced to express the deficient ATCF factor and reimplanted into the host. Alternatively, somatic cell gene therapy may be effected by directly injecting a vector bearing the desired gene into the individual, in vivo, whereby the gene will be delivered and expressed by host tissue.

Vectors/methods that may be used to deliver the above-identified nucleotides to the individual may include, but are not limited to, liposomal or lipid-associated delivery, direct injection of nucleotides encoding the desired products, viral mediated delivery, and the like.

Recombinant retroviruses have been widely used in gene transfer experiments (see generally, Mulligan, R. C., Chapter 8, *In: Experimental Manipulation of Gene Expression*, Academic Press, pp. 155–173 (1983); Coffin, J., *In: RNA Tumor Viruses*, Weiss, R. et al. (eds.), Cold Spring Harbor Laboratory, Vol. 2, pp. 36–38 (1985). One of ordinary skill will realize that nucleotides encoding any of the above-mentioned factors may be introduced using retroviral vectors; however, for purposes of illustration, the contemplated use of the ATCF gene will be described and should not be construed as limiting in any way.

Retroviral systems will typically insert the ATCF gene downstream from the LTR or other exogenous promotor element in a replication defective retroviral vector. Alternatively, the endogenous promoter may also be inserted into the vector. The ATCF-containing vector may be constructed such that the initiation codon of the ATCF gene functionally replaces the AUG initiation codon of the retroviral gag gene. This arrangement retains the retroviral mRNA splice donor and acceptor sequences as well as the normal viral regions that control the initiation of translation.

Typically, the above construct will be introduced into a suitable retroviral packaging cell line that will provide the viral proteins necessary to construct infectious virus which, preferably exclusively, contain the recombinant retroviral/ATCF genome. The packaging cell line will preferably provide viral envelope proteins which allow the infection, and hence delivery and expression of the ATCF gene, of the desired host cells.

Other eucaryotic viruses which may be used as vectors to transduce mammalian cells include adenovirus, papilloma virus, herpes virus, adeno-associated virus, rabies virus, and the like (See generally, Sambrook et al., *Molecular Cloning*, Cold Spring Harbor Laboratory Press, Cold Spring Harbor, N.Y., Vol. 3:16.1–16.89 (1989).

Compositions comprising ATCFs, MIFs, SIFs, or biologically active derivatives thereof, may also find application as ingredients or medicinal components of cosmetic or topical compositions.

5.1. Purification of AT Complementing, SIF and MIF Factors

AT complimenting factor activity was initially observed using cocultured normal and AT-fibroblasts which had been γ-irradiated. The cocultivation studies indicated that diffusible factors were able to complement AT cells. Subsequent to the initial observation, SIF and MIF activity was found in sonicates prepared from irradiated normal fibroblasts.

Purification of the subject diffusible factors may be conducted using any of a number of variations of well established biochemical and molecular biology techniques. Such techniques are well known to those of ordinary skill in the biochemical arts and have been extensively described in references such as Berger and Kimmel, *Guide to Molecular Cloning Techniques, Methods in Enzymology*, Volume 152, Academic Press, San Diego, Calif. (1987; *Molecular Cloning: A Laboratory Manual,* 2d ed., Sambrook, J., Fritsch, E. F., and Maniatis, T. (1989); *Current Protocols in Molecular Biology*, John Wiley & Sons, all Vols., 1989, and periodic updates thereof); *New Protein Techniques: Methods in Molecular Biology,* Walker, J. M., ed., Humana Press, Clifton, N.J., 1988; and *Protein Purification: Principles and Practice,* 3rd. Ed., Scopes, R. K., Springer-Verlag, New York, N.Y., 1987. In general, techniques including, but not limited to, ammonium sulfate precipitation, centrifugation, ion exchange, gel filtration, and reverse-phase chromatography (and the HPLC or FPLC forms thereof) may be used to purify ATCF, MIF or SIF activity.

Alternatively, the anti-SIF, anti-MIF, DRF or ATCF antibody of Section 5.3. may be used to purify SIF or MIF by affinity chromatography.

5.2. Assays for AT Complementing, SIF and MIF Activity

Several assays were used to detect ATCF activity. One assay was based on the observation that, in culture, ATCF provided AT cells with enhanced resistance to ionizing radiation. Another assay directly tested ATCF's ability to inhibit post-irradiation DNA synthesis in AT cells, and yet another assay directly tested SIF-factor's ability to arrest DNA synthesis in non-irradiated normal (non-AT) cells. Another assay tested MIFs ability to inhibit mitosis in normal cells.

5.3. Anti-SIF, DRF, and AT-C Antibodies

The invention is also directed to polyclonal and monoclonal antibodies which recognize epitopes of SIF, MIF, DRF, and ATCF polypeptides. SIF, MIF, DRF, and ATCF factors for use in the induction of antibodies of interest need not be biological active; however, SIF, MIF, DRF, and ATCF-factors for use in the induction of antibodies will necessarily have immunological activity.

Given that similar methodologies may be applied to the generation of antibodies to SIF, MIF, DRF, and ATCF polypeptides, for purposes of convenience, only the SIF factor antibodies will be discussed.

Polypeptides for use in the induction of SIF-factor-specific antibodies may have an amino acid sequence consisting of at least five amino acids, preferably at least 10 amino acids, mimicking a portion of the amino acid sequence of SIF-factor, and may contain the entire amino acid sequence of naturally occurring SIF or a SIF-derivative.

Anti-SIF antibodies are expected to have a variety of medically useful applications, several of which are described generally below. More detailed and specific descriptions of various uses for anti-SIF antibodies are provided in the sections and subsections which follow. Briefly, anti-SIF antibodies may be used for the detection and quantification of SIF polypeptide expression in cultured cells, tissue samples, and in vivo. Such immunological detection of SIF may be used, for example, to identify, monitor, and assist in the prognosis of neoplasms characterized by aberrant or attenuated SIF expression and/or function. Additionally, monoclonal antibodies recognizing epitopes from different parts of the SIF structure may be used to detect and/or distinguish between native SIF and various subcomponent and/or mutant forms of the molecule. Anti-SIF antibody preparations are also envisioned as useful biomodulatory agents capable of effectively treating particular human cancers. In addition to the various diagnostic and therapeutic utilities of anti-SIF antibodies, a number of industrial and research applications will be obvious to those skilled in the art, including, for example, the use of anti-SIF antibodies as affinity reagents for the isolation of SIF polypeptides, and as immunological probes for elucidating the biosynthesis, metabolism and biological functions of SIF.

Anti-SIF antibodies may be useful for influencing cell functions and behaviors which are directly or indirectly mediated by SIF. As an example, modulation of SIF biological activity with anti-SIF antibodies may influence the SIF-mediated inhibition of DNA synthesis and, as a consequence, modulate intracellular signals generated in response to SIF. In this regard, anti-SIF antibodies may be useful to effectively block ligand-induced, SIF-mediated activation of the SIF receptor. Conversely, anti-SIF antibodies capable of acting as SIF ligands may be used to trigger SIF biological activity and/or initiate a ligand-induced, SIF-mediated effect on cellular DNA synthesis.

In another embodiment, this invention includes antibodies capable of binding to SIF or the SIF receptor and modulating SIF functionality, thereby affecting a response in the target cell. Various procedures known in the art may be used for the production of polyclonal antibodies to epitopes of SIF. For the production of polyclonal antibodies, a number of host animals are acceptable for the generation of anti-SIF antibodies by immunization with one or more injections of a SIF polypeptide preparation, including but not limited to rabbits, mice, rats, etc. Various adjuvants may be used to increase the immunological response in the host animal, depending on the host species, including but not limited to Freund's (complete and incomplete adjuvant), mineral gels such as aluminum hydroxide, surface active substances such as lysolecithin, pluronic polyols, polyanions, oil emulsions, keyhole limpet hemocyanins, dinitrophenol, and potentially useful human adjuvants such as BCG (bacille Calmette-Guerin) and *Corynebacterium darvum*.

A monoclonal antibody to an epitope of SIF may be prepared by using any technique which provides for the production of antibody molecules by continuous cell lines in culture. These include, but are not limited to, the hybridoma technique originally described by Kohler and Milstein (1975, *Nature* 256:495–497), and the more recent human B-cell hybridoma technique (Kosbor et al., 1983, *Immunology Today* 4:72) and EBV-hybridoma technique (Cole et al., 1985, Monoclonal Antibodies and Cancer Therapy, Alan R. Liss, Inc., pp. 77–96). In addition, techniques developed for the production of "chimeric antibodies" by splicing the genes from a mouse antibody molecule of appropriate antigen specificity together with genes from a human antibody molecule of appropriate biological activity may be used (Morrison et al., 1984, *Proc. Natl. Acad. Sci.* 81:6851–6855; Neuberger et al., 1984, *Nature* 312:604–608; Takeda et al., 1985, *Nature* 314:452–454). Alternatively, techniques described for the production of single chain antibodies (U.S. Pat. No. 4,946,778) can be adapted to produce SIF-specific single chain antibodies. Recombinant human or humanized versions of anti-SIF monoclonal antibodies are a preferred embodiment for human therapeutic applications. Humanized antibodies may be prepared according to procedures in the literature (e.g., Jones et al., 1986, Nature 321:522–25; Reichman et al., 1988, *Nature* 332:323–27; Verhoeyen et al., 1988, *Science* 239:1534–36).

The recently described "gene conversion mutagenesis" strategy for the production of humanized anti-HER2 monoclonal antibody may also be employed in the production of humanized anti-SIF antibodies (Carter et al., 1992, *Proc. Natl. Acad. Sci. U.S.A.* 89:4285–89). Alternatively, techniques for generating a recombinant phage library of random combinations of heavy and light regions may be used to prepare recombinant anti-SIF antibodies (e.g., Huse et al., 1989, *Science* 246:1275–81).

As an example, anti-SIF monoclonal antibodies may be generated by immunization of mice with cells selectively overexpressing SIF receptor or with partially purified recombinant SIF polypeptides. In one embodiment, the full length SIF receptor polypeptide may be expressed in Baculovirus systems, and membrane fractions of the recombinant cells used to immunize mice. Hybridomas are then screened on CHO cells which express the SIF receptor protein to identify monoclonal antibodies reactive with the extracellular domain of the SIF receptor. Such monoclonal antibodies may be evaluated for their ability to block SIF factor; or for their ability to bind to the SIF receptor and stay resident on the cell surface, or to be internalized into cells expressing SIF receptor; or for their ability to directly upregulate or downregulate the SIF mediated signal transduction cascade, and/or to directly induce a SIF-mediated signal resulting in modulation of cellular DNA synthesis.

In yet another embodiment, a soluble recombinant SIF-Immunoglobulin (SIF-Ig) fusion protein is expressed and purified on a Protein A affinity column. The soluble SIF-Ig fusion protein may then be used to screen phage libraries designed so that all available combinations of a variable domain of the antibody binding site are presented on the surfaces of the phages in the library. Recombinant anti-SIF antibodies may be propagated from phage which specifically recognize the SIF-Ig fusion protein.

Antibody fragments which contain the idiotype of the molecule may be generated by known techniques. For example, such fragments include but are not limited to: the F(ab)'E2 fragment which can be produced by pepsin digestion of the intact antibody molecule; the Fab' fragments which can be generated by reducing the disulfide bridges of the F(ab')2 fragment, and the two Fab fragments which can be generated by treating the antibody molecule with papain and a reducing agent. Alternatively, Fab expression libraries may be constructed (Huse et al., 1989, *Science* 246:1275–1281) to allow rapid and easy identification of monoclonal Fab fragments with the desired specificity to SIF protein.

5.4. Cloning and Expression of the ATCF, DRF, MIF and SIF Genes

Production of SIF, MIF, ATCF, and DRF polypeptides using recombinant DNA technology may be divided into a four-step process: (1) isolation or generation of DNA encoding the desired polypeptide; (2) construction of an expression vector capable of directing the synthesis of the desired polypeptide; (3) transfection or transformation of appropriate host cells capable of replicating and expressing the SIF, MIF, ATCF or DRF coding sequence and/or processing the initial product to produce the desired polypeptide; and (4) identification and purification of the desired product.

Given that one of ordinary skill will realize that similar methodologies apply to the expression of SIF, MIF, DRF, and ATCF polypeptides, for purposes of convenience, only the cloning and expression of SIF factor will be specifically discussed.

5.4.1. Isolation or Generation of SIF Encoding DNA

Edman degradation may be used on purified SIF protein, or purified oligopeptide portions thereof, to generate amino acid sequence data which may be "reverse-translated" to produce a population of hypothetical SIF-encoding oligonucleotide probes for use in screening cDNA libraries.

Given that degenerate oligonucleotide screening may not provide a reasonable expectation of success, one may alternatively choose to use the amino acid sequence data to screen any of several sequence databases. The Swiss/Prot or the NBRF Protein database are examples of databases where one might find homologous polypeptides, and the Genbank database is exemplary of a DNA sequence database. Given the widespread introduction of expressed sequence tags (ESTs) into sequence databases, many databases contain partial sequences for which there are no known function. To the extent that one reading frame of a given EST matches the query sequence, the remainder of the EST sequence would probably serve as an ideal probe for obtaining a full length copy of the cDNA encoding the query protein.

Once obtained, the SIF-encoding DNA, or functional equivalents thereof, may be used to construct recombinant expression vectors which will direct the expression of the desired SIF polypeptide product. In one embodiment, DNA encoding the SIF polypeptide, or fragments or functional equivalents thereof, may be used to isolate or generate recombinant molecules which will direct the expression of the recombinant SIF product in appropriate host cells. The anti-SIF antibody discussed in Section 5.3., supra, may be used to verify and identify clones expressing all or a portion of the SIF gene.

SIF-encoding nucleotide sequences may be obtained from any of the variety of cell sources (described above) which produce SIF-like activities and/or which express SIF-encoding mRNA. For example, SIF-encoding cDNAs may be obtained from HeLa cells, infra. In addition, a number of human cell sources may also be suitable for obtaining SIF cDNAs, including but not limited to HL-60 cells.

The SIF coding sequence may be obtained by molecular cloning from RNA isolated and purified from such cell sources or by genomic cloning. Either cDNA or genomic libraries of clones may be prepared using techniques well known in the art and may be screened for particular SIF-encoding DNAs with nucleotide probes which are substantially complementary to any portion of the SIF gene. Alternatively, cDNA or genomic DNA may be used as templates for PCR cloning with suitable oligonucleotide primers. Full length clones, i.e., those containing the entire coding region of the desired SIF may be selected for constructing expression vectors, or overlapping cDNAs may be ligated together to form a contiguous coding sequence. Alternatively, SIF-encoding DNAs may be synthesized in whole or in part by chemical synthesis using techniques standard in the art.

5.4.2. Construction of SIF Expression Vectors

Various expression vector/host systems may be utilized equally well by those skilled in the art for the recombinant expression of SIF polypeptides. Such systems include, but are not limited to, microorganisms such as bacteria transformed with recombinant bacteriophage DNA, plasmid DNA or cosmid DNA expression vectors containing the desired SIF coding sequence; yeast transformed with recombinant yeast expression vectors containing the desired SIF coding sequence; insect cell systems infected with recombinant virus expression vectors (e.g., sf9 cells and baculovirus) containing the desired SIF coding sequence; plant cell systems infected with recombinant virus expression vectors (e.g., cauliflower mosaic virus CaMV; tobacco mosaic virus, TMV) or transformed with recombinant plasmid expression vectors (e.g., Ti plasmid) containing the desired SIF coding sequence; or animal cell systems infected with recombinant virus expression vectors (e.g., adenovirus, vaccinia virus) including cell lines engineered to contain multiple copies of the SIF DNA either stably amplified (e.g., CHO/dhfr, CHO/glutamine synthetase) or unstably amplified in double-minute chromosomes (e.g., murine cell lines).

The expression elements of these vectors vary in their strength and specificities. Depending on the host/vector system utilized, any one of a number of suitable transcription and translation elements may be used. For instance, when cloning in mammalian cell systems, promoters isolated from the genome of mammalian cells, (e.g., mouse metallothionein promoter) or from viruses that grow in these cells, (e.g., vaccinia virus 7.5K promoter or Moloney murine sarcoma virus long terminal repeat) may be used. Promoters produced by recombinant DNA or synthetic techniques may also be used to provide for transcription of the inserted sequences.

Specific initiation signals are also required for sufficient translation of inserted protein coding sequences. These signals include the ATG initiation codon and adjacent sequences. In cases where the entire SIF gene including its own initiation codon and adjacent sequences are inserted into the appropriate expression vectors, no additional translational control signals may be needed. However, in cases where only a portion of the coding sequence is inserted, exogenous translational control signals, including the ATG initiation codon, must be provided. Furthermore, the initiation codon must be in phase with the reading frame of the SIF coding sequences to ensure translation of the entire insert. These exogenous translational control signals and initiation codons can be of a variety of origins, both natural and synthetic. The efficiency of expression may be enhanced by the inclusion of transcription attenuation sequences, enhancer elements, etc.

For example, in cases where an adenovirus is used as a vector for driving expression in infected cells, the desired SIF coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E3 or E4) will result in a recombinant virus that is viable and capable of expressing SIF in infected hosts. Similarly, the vaccinia 7.5K promoter may be used.

An alternative expression system which could be used to express SIF is an insect system. In one such system, *Autographa californica* nuclear polyhidrosis virus (AcNPV) is used as a vector to express foreign genes. The virus grows in *Spodoptera frugiperda* cells. The SIF coding sequence may be cloned into non-essential regions (for example the polyhedrin gene) of the virus and placed under control of an AcNPV promoter (for example the polyhedrin promoter). Successful insertion of the SIF coding sequence will result in inactivation of the polyhedrin gene and production of non-occluded recombinant virus (i.e., virus lacking the proteinaceous coat encoded by the polyhedrin gene). These recombinant viruses are then used to infect *Spodoptera frugiperda* cells in which the inserted gene is expressed. Yet another approach uses retroviral vectors prepared in amphotropic packaging cell lines, which permit high efficiency expression in numerous cell types. This method allows one to assess cell-type specific processing, regulation or function of the inserted protein coding sequence.

In addition, a host cell strain may be chosen which modulates the expression of the inserted sequences, or modifies and processes the gene product in the specific fashion desired. Expression from certain promoters can be elevated in the presence of certain inducers (e.g., zinc and cadmium ions for metallothionein promoters). Therefore, expression of the recombinant SIF polypeptide may be controlled. This is important if the protein product of the cloned foreign gene is lethal to host cells. Furthermore, modifications (e.g., phosphorylation) and processing (e.g., cleavage) of protein products are important for the function of the protein. Different host cells have characteristic and specific mechanisms for the post-translational processing and modification of protein. Appropriate cell lines or host systems can be chosen to ensure the correct modification and processing of the foreign protein to be expressed.

5.4.3. Transformants Expressing SIF Gene Products

The host cells which contain the recombinant coding sequence and which express the desired SIF polypeptide product may be identified by at least four general approaches (a) DNA—DNA, DNA—RNA or RNA-antisense RNA hybridization; (b) the presence or absence of "marker" gene functions; (c) assessing the level of transcription as measured by the expression of SIF mRNA transcripts in the host cell; and (d) detection of the SIF product as measured by immunoassay and, ultimately, by its biological activities.

In the first approach, for example, the presence of SIF coding sequences inserted into expression vectors can be detected by DNA—DNA hybridization using hybridization probes and/or primers for PCR reactions comprising polynucleotides that are homologous to the SIF coding sequence.

In the second approach, the recombinant expression vector/host system can be identified and selected based upon the presence or absence of certain "marker" gene functions (e.g., thymidine kinase activity, resistance to antibiotics, resistance to methotrexate (MTX), resistance to methionine sulfoximine (MSX), transformation phenotype, occlusion body formation in baculovirus, etc.). For example, if the SIF coding sequence is inserted within a marker gene sequence of the vector, recombinants containing that coding sequence can be identified by the absence of the marker gene function. Alternatively, a marker gene can be placed in tandem with the SIF sequence under the control of the same or different promoter used to control the expression of the SIF coding sequence. Expression of the marker in response to induction or selection indicates expression of the SIF coding sequence. In a particular embodiment described by way of example herein, a SIF expression vector incorporating glutamine synthetase as a selectable marker is constructed, used to transfect CHO cells, and amplified expression of SIF in CHO cells is obtained by selection with increasing concentrations of MSX.

In the third approach, transcriptional activity for the SIF coding region can be assessed by hybridization assays. For example, polyadenylated RNA can be isolated and analyzed by Northern blot using a probe homologous to the SIF coding sequence or particular portions thereof. Alternatively, total nucleic acids of the host cell may be extracted and assayed for hybridization to such probes.

In the fourth approach, the expression of SIF can be assessed immunologically, for example by Western blots, immunoassays such as radioimmunoprecipitation, enzyme-linked immunoassays and the like. Alternatively, expression of SIF may be assessed by detecting a biologically active product. Where the host cell secretes the gene product, the cell free media obtained from the cultured transfectant host cell may be assayed for SIF activity. Where the gene product is not secreted, cell lysates may be assayed for such activity. In either case, assays which measure ligand binding to SIF, SIF phosphorylation, or other bioactivities of SIF may be used.

5.4.4. Purification of Recombinantly Expressed SIFs

Given the large quantity of SIF protein produced by recombinant expression, it is presumed that one would understand that the methods described in Section 5.1., supra, as well as general biochemical techniques, could be used or suitably modified to allow the purification of the recombinantly produced protein.

5.5. ATCF, MIF and SIF-Ligands

It is likely that the claimed factors correspond to naturally produced ligands for any of a variety of cellular receptors. The factors may thus prove useful for the identification and cloning of a novel class of cell surface receptors which are involved in cellular signaling pathways which retard or arrest DNA synthesis, or affect the transition from the $G_2$-phase of the cell cycle to mitosis. Thus, an additional aspect of the present invention is directed to ATCF, SIF and MIF ligands. As used herein, the subject ATCF, SIF or MIF ligands include all molecules capable of competitively binding ATCF, SIF or MIF factor or functional analogues thereof. Functional analogues of ATCF, SIF or MIF-ligands are capable of activating the ATCF, SIF or MIF-associated cell signaling pathways involved in inhibiting either the synthesis of cellular DNA, or cell division. The subject ATCF, SIF or MIF ligands may comprise, but are not limited to, membrane-bound cellular receptors; soluble proteins/polypeptides, or peptide or oligopeptide portions thereof; small organic molecules; glycoproteins; or polysaccharides. Where the ATCF, SIF or MIF ligand is a cell membrane protein, activation of intracellular cellular kinase activity may stimulate ATCF, SIF or MIF-ligand autophosphorylation and may affect a biological activity mediated by ATCF, SIF or MIF.

The ATCF, SIF or MIF ligands of the present invention may be prepared by synthetic or recombinant means, or may be isolated from natural sources. The ATCF, SIF or MIF ligands of the present invention may also contain deletions, additions or substitutions of amino acid residues as long as the ligand maintains ATCF, SIF or MIF binding and cell signal activation capacity. Such amino acid substitutions may be made on the basis of similarity in polarity, charge, solubility, hydrophobicity, hydrophilicity and/or the amphipathic nature of the resides involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine.

In vitro polypeptide synthesis may be performed using manual techniques or by automation. Automated synthesis may be achieved, for example, by using an Applied Biosystems 431A Peptide Synthesizer (Foster City, Calif.) and following the instructions provided in the instruction manual supplied by the manufacturer.

5.6. Anti-ATCF, SIF and MIF Ligand Antibodies

The present invention is also directed to polyclonal and monoclonal antibodies which recognize epitopes of ATCF, SIF or MIF ligand polypeptides. Anti-ATCF, SIF and MIF ligand antibodies are expected to have a variety of useful medical applications. Briefly, anti-ATCF, SIF or MIF ligand antibodies may be used for the detection and quantification of ATCF, SIF or MIF ligand polypeptide expression in cultured cells, tissue samples, and in vivo. For example, monoclonal antibodies recognizing epitopes from different parts of the ATCF, SIF or MIF ligand structure may be used to detect and/or distinguish binding from non-binding regions of the ligand.

Anti-SIF ligand antibody preparations are also envisioned as useful biomodulatory agents capable of effectively treating particular human cancers. An anti-SIF ligand antibody could be used to block signal transduction mediated through SIF, thereby inhibiting undesirable biological responses.

In addition to the various diagnostic and therapeutic utilities of anti-ATCF, SIF or MIF ligand antibodies, a number of industrial and research applications will be obvious to those skilled in the art, including, for example, the use of anti-ATCF, SIF or MIF ligand antibodies as affinity reagents for the purification of SIF and MIF-ligand polypeptides, and as immunological probes for elucidating the biosynthesis, metabolism and biological functions of ATCF, SIF or MIF ligands.

Anti-SIF and MIF ligand antibodies may be useful for influencing cell functions and behaviors which are directly or indirectly mediated by SIF or MIF, respectively. As an example, modulation of SIF biological activity with anti-SIF ligand antibodies (which may compete with SIF while not activating the receptor) may influence SIF receptor-mediated activation and, as a consequence, modulate intracellular signals generated by the receptor.

Alternatively, to the extent that they may bind the SIF receptor and trigger a SIF-like activity, anti-SIF ligand antibodies may be also useful as substitutes for SIF activity. This activity may be especially important given that suitably constructed (e.g., "humanized") anti-SIF receptor antibodies will likely exhibit a different in vivo stability and half-life. Various procedures known in the art may be used for the production of antibodies to epitopes of the ATCF, SIF or MIF ligands (see Section 5.3., supra). It is contemplated that anti-ATCF, SIF or MIF ligand antibodies will facilitate the isolation and recombinant expression of genes encoding the respective ligands by allowing for the screening of appropriately constructed expression libraries.

5.7. Cloning of SIF Ligand DNA

Given that similar methodologies may be used to clone and express SIF, MIF, ATCF, or DRF ligands, for purpose of convenience, only the SIF ligand will be further discussed. SIF ligand-encoding nucleic acid sequences may be obtained from cell lines, including, but not limited to, AT or HeLa cells or any other cell source capable of producing an activity capable of binding to a SIF factor.

Given that SIF-ligands bind SIFs, SIF ligands may be used as competitive inhibitors of the SIF binding assays described above and below. Thus, one of ordinary skill would understand that the methods described for assaying for SIF activity, disclosed in Sections 6.3.–6.5., infra may also be adapted to assay for SIF-ligand activity.

The techniques disclosed in Sections 5.4.–5.4.4, supra, also apply to the construction of SIF ligand expression vectors and identification of recombinant transformants expressing SIF ligand gene products.

5.8. Recombinant Expression of SIF-Ligands

As above, since similar methodologies may be used to obtain recombinant expression of SIF, ATCF, MIF or DRF, only the expression of SIF will be further discussed. When proteinaceous, the SIF-ligands of the present invention may be produced by the cloning and expression of DNA encoding the desired SIF ligand. Such DNA may be ligated into a number of expression vectors well known in the art and suitable for use in a number of acceptable host organisms, in fused or mature form, and may contain a signal sequence to permit secretion. Both procaryotic and eucaryotic host expression systems may be employed in the production of recombinant SIF ligands. For example, a SIF ligand precursor coding sequence or its functional equivalent may be used in a host cell capable of processing the precursor correctly. Alternatively, the coding sequence for a mature SIF ligand may be used to directly express the mature SIF ligand molecule. Functional equivalents of the SIF ligand precursor coding sequence include any DNA sequence which, when expressed inside the appropriate host cell, is capable of directing the synthesis, processing and/or export of the SIF ligand.

The examples below are provided to illustrate the subject invention. These examples are provided by way of illustration and are not included for the purpose of limiting the invention.

EXAMPLES

6.0. Coincubation Studies

Coincubation studies were conducted to determine whether or not an irradiation induced diffusible factor may correct irradiation related abnormalities in AT cells. In these experiments, log phase cultures of AT cells were seeded onto sterile glass coverslips at an approximate density of about $10^4/cm^2$ and placed in 100 mm culture dishes which had been pre-inoculated with approximately $5 \times 10^5$ feeder cells. This arrangement prevented cell-to-cell contact between the test cells on the coverslip and the feeder cells on the plate. The two cells were coincubated for 2–3 days after which they were used in tests to determine whether a diffusible factor produced by the feeder cells may influence the growth characteristics of the AT cells.

6.0.1. Assay for Partial Remedy of the Radiosensitivity of AT Cells In Vitro Because of defects in post-irradiation DNA repair mechanisms, AT cells generally display a heightened sensitivity to irradiation. To test whether an irradiation-induced diffusible factor renders AT cells significantly less radiosensitive, normal and AT fibroblasts were coincubated as described above. After two to three days of coincubation, the cells were irradiated with 2, 4, and 6 Gy. The cells were allowed to sit for four to eight hours after which the AT cells were trypsinized and tested for colony forming ability.

Figure 1:
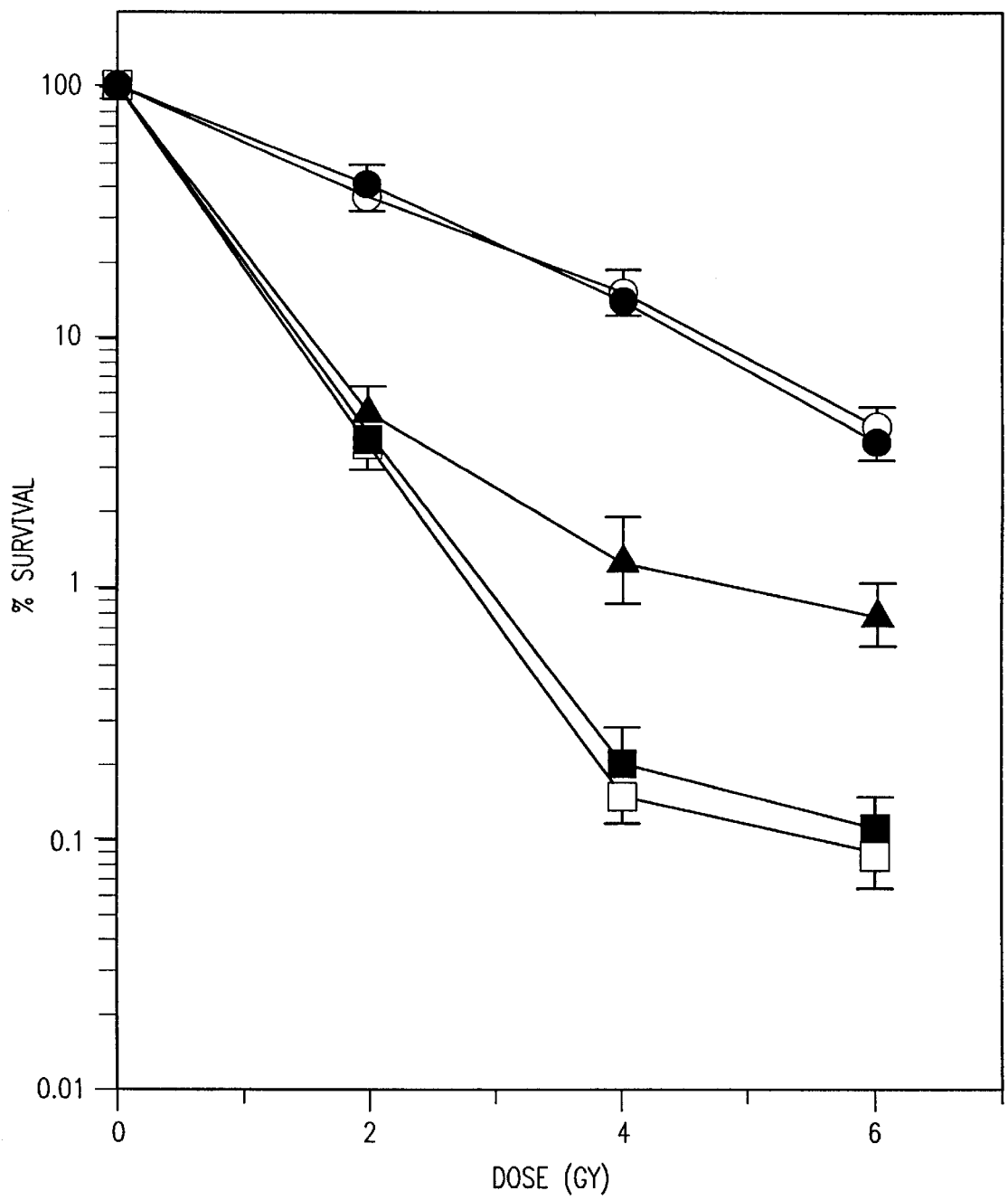
Figure 2:
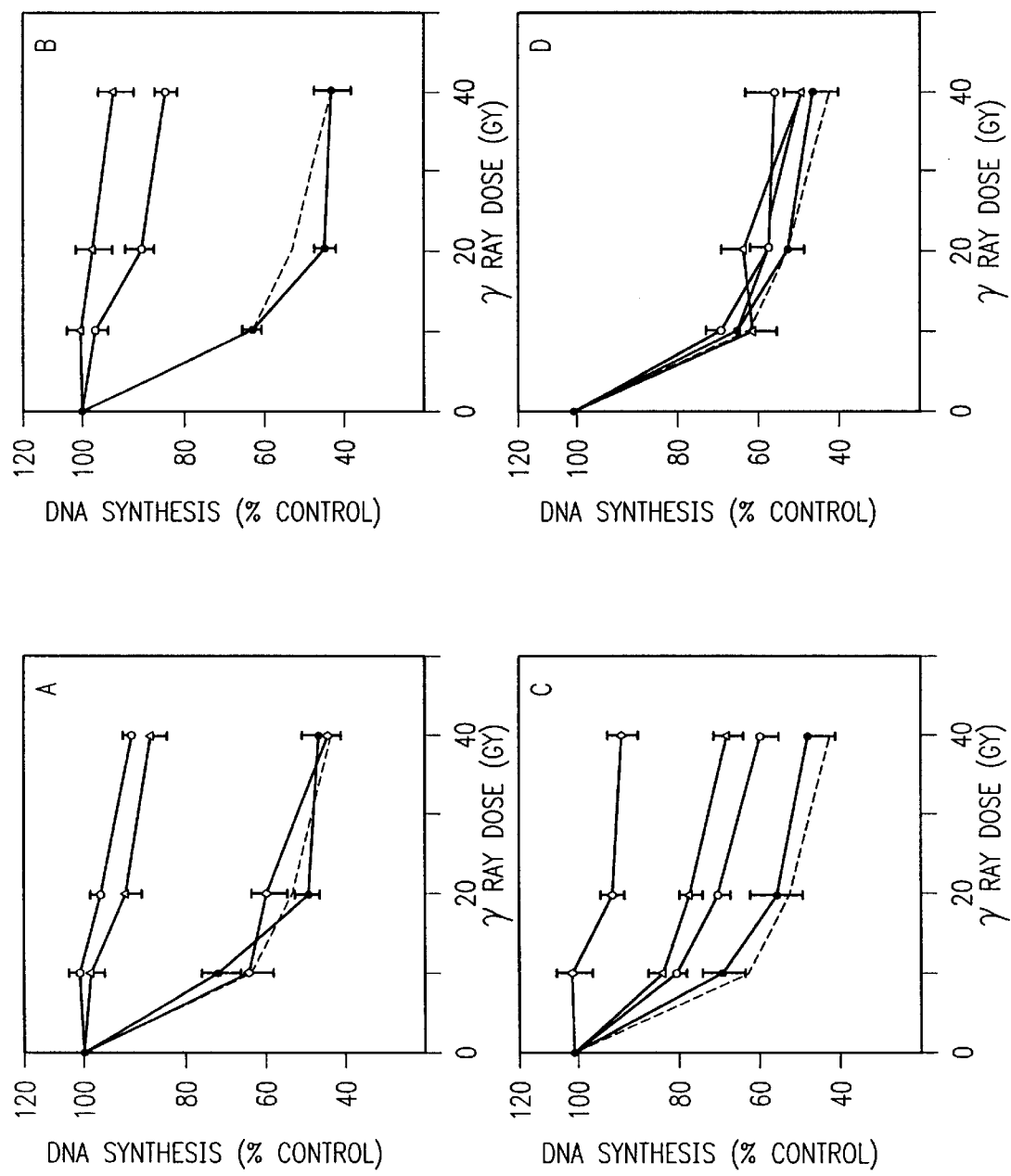

These data are presented in FIG. 1, and indicate that a diffusible factor (ATCF) produced by normal cells provides significant protection to irradiated AT cells (compare solid triangles to squares).

6.0.2. Assay for In Vitro Inhibition of DNA Synthesis in AT Cells

The radioresistant DNA synthesis trait is the molecular signature of AT fibroblasts, and may be fully rectified by coincubation with normal cells. After coincubation (see Section 6.0., supra) for 2–3 days, the cultures were exposed (without changing medium) to varying doses of γ-irradiation. After irradiation, the cells were incubated for 1 hr in the original growth medium, and subsequently pulse-labeled for 15 minutes using medium containing $3.7 \times 10^4$ Bq [methyl-$^3$H]dthymidine (specific activity, $2.4 \times 10^{11}$ Bq/mmol) per ml. The cells were rinsed with PBS, fixed, and the coverslips were mounted on glass microscope slides. The cells were then dipped in liquid Kodak NTB-2 nuclear track emulsion, dried, exposed at 420 C. for 7 days, and finally developed in Kodak D19 developer. The number of silver grains above the nucleus of S-phase cells was determined using an automated image analyzer. The normalized number of silver grains above the nucleus indicated the extent of DNA synthesis in the culture (see generally: Murname, J. P. and Painter, R. B., 1982, *Proc. Natl. Acad. Sci. USA* 79:1960–1963; Jaspers, N. G. J. and Bootsma, D., 1982, Mutat. Res. 92:439–448).

The results of these experiments are shown in FIGS. 2a–d. The data in FIGS. 2a–d shows that AT cells cocultivated with either a complementary AT group (e.g., AT group A complements AT group D), or normal cells have markedly reduced levels of radioresistant DNA synthesis (RDS).

6.1. Purification of ATCF, SIF and MIF Factors

ATCF is prepared using medium conditioned by growth of HL-60 cells and an adaptation of the protocol used by Akagi et al., 1987, *Cancer Res.* 47:4086. Generally, cells may be grown to the desired density using a Nunc cell factory, or other suitable culture methods. Briefly, HL-60 cells will be grown in suspension in RPMI 1640 for 48 hr, rinsed and incubated with serum-free medium (DM 1:1 mixture of RPMI and Ham's F-12) for 24 hr, after which the conditioned serum-free medium will be centrifuged, and the ATCF in the supernatant concentrated about 1000-fold. The sample may then be lyophilized and stored prior to subsequent purification steps. After reconstitution, the medium is fractionated using size exclusion HPLC or FPLC, after which the fractions are assayed for ATCF activity using in situ autoradiography. The ATCF containing fractions are pooled and subsequently purified using ion exchange chromatograph [Accel QMA (anionic) or carboxymethylcellulose, CM (cationic)], affinity chromatograph (Con A-Sepharose), and gel filtration (Sephadex G-75).

Normal fibroblasts (e.g. HeLa or HL-60 cells) were seeded onto culture flasks (or inoculated into Spinner flasks for growth in suspension) at a suitable density in the indicated medium. After several days of growth, the cells were subject to between about 1 and about 6 Gy of irradiation. Twenty four hours after irradiation, the cells were gathered from the culture flasks, chilled and, optionally, sonicated to release SIF, MIF and DRF factors. After sonication, the sonicates were centrifuged to remove whole cells and cellular debris. The supernatant containing SIF and MIF activity was collected, assayed for SIF, DRF and MIF activity, and stored at 4° C. SIF, DRF and MIF activities obtained in this manner remained stable for at least two months at 4° C. Pooled preparations were used as starting materials for subsequent biochemical purifications.

The DNA synthesis inhibition assay described in Section 6.2., infra, is used throughout the purification procedure in order to determine which purification/column fractions inhibit DNA synthesis.

Ten liters of SIF and MIF-factor containing medium are concentrated 16-fold using an Amicon ultrafiltration unit (3,500 molecular weight cutoff membrane), and subjected to sequential precipitation with increasing concentrations of ammonium sulfate. After centrifugation, the supernatant is extensively dialyzed against PBS and passed through a DEAE-sepharose (Pharmacia) column pre-equilibrated with PBS. The flow-through fraction is then applied onto a 4 ml heparin-acrylic (Bio-Rad) column equilibrated with PBS. DNA synthesis inhibiting activity eluted from the heparin column between 0.2 and 0.8 M NaCl. Active column fractions are pooled, ammonium sulfate precipitated, centrifuged at 12,000×g for 5 min, and the resulting supernatant is collected, dialyzed, and assayed for the ability to inhibit DNA synthesis in normal or AT cells (see below).

The MIF factor was also identified in whole cell extracts prepared from human tumor (HeLa) cells which had been exposed to 40 Gy γ radiation and incubated for 0.5 hour prior to cell lysis. The MIF is heat-stable and is retained after dialysis in a bag with a pore size of about 3500 molecular weight cutoff.

6.2. Assay for SIF-Mediated Inhibition of DNA Synthesis in Normal Cells In Vitro Cultures of normal (non-AT) human fibroblasts and hematological cells were grown and labeled essentially as outlined in Section 6.4. After 18–20 hours of growth in $^{14}$C-Thd (thymidine) containing medium, SIF extract was added to the cells and the cells were pulse-labeled with $^3$H-Thd. The resulting levels of DNA synthesis were calculated by determining the relative extent of $^3$H-Thd incorporation after initial exposure to SIF extract (by scintillation counting). Alternatively, the cells were $^3$H-labeled and the number of exposed silver grains above the nucleus were counted as discussed above. The data were normalized relative to control cultures and calculated as a function of the concentration of SIF extract used, or a timecourse of the amount of DNA synthesis was tracked over the hours following SIF addition. These data are presented in FIGS. 3, 4, and 5.

Figure 3:
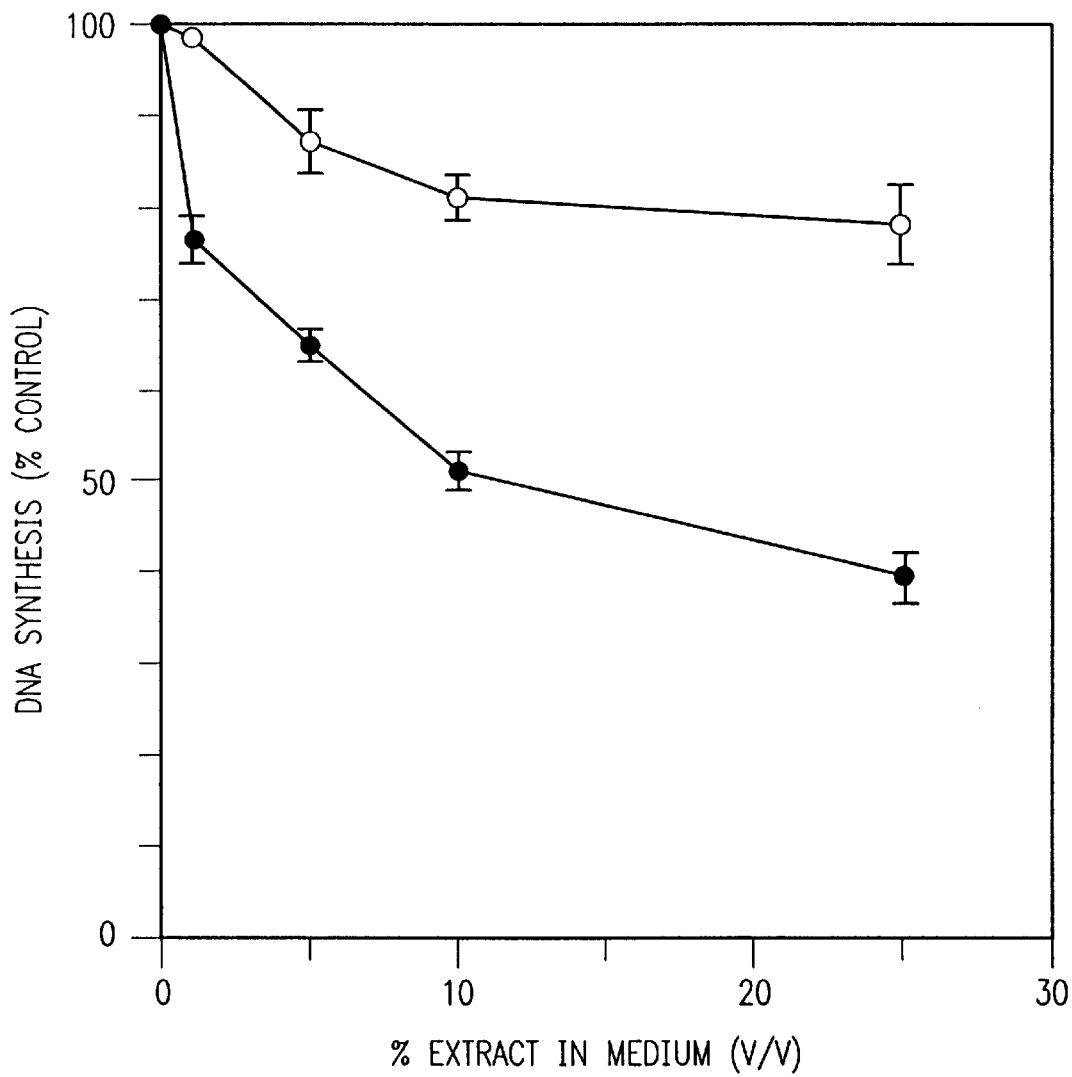

The data in FIG. 3 show that the level of SIF activity is reduced, but not totally abrogated, after the SIF extract is boiled for 10 minutes (open circles). These data indicate that at least a portion of the SIF inducing factors in the SIF extract is heat stable.

Figure 4:
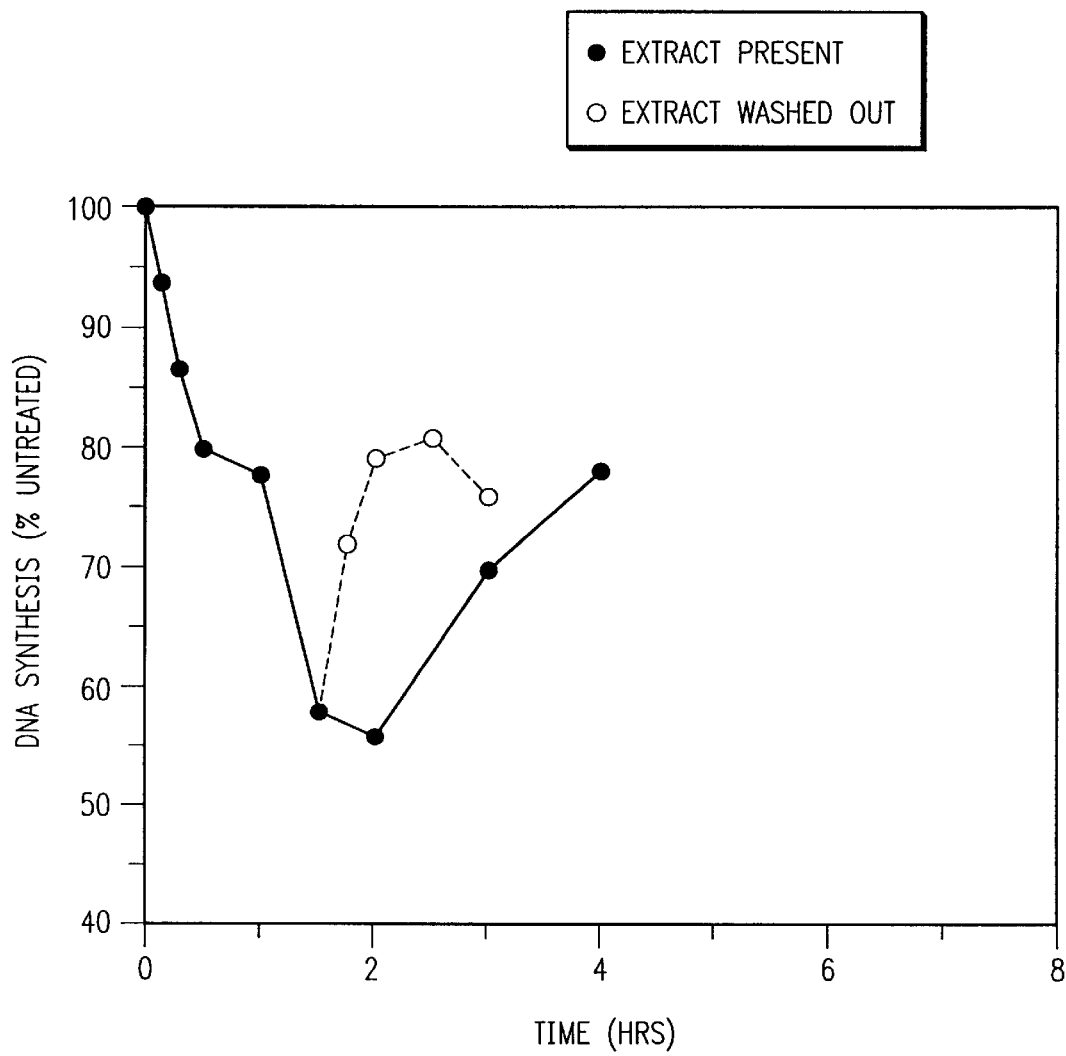
FIGS. 4 and 5 show time-course data which indicate that SIF-mediated repression of DNA synthesis is reversible. The normalized percent of DNA synthesis (measured on a per adherent cell basis) jumps markedly after SIF factor is washed-out of the medium (dashed lines).
Figure 5:
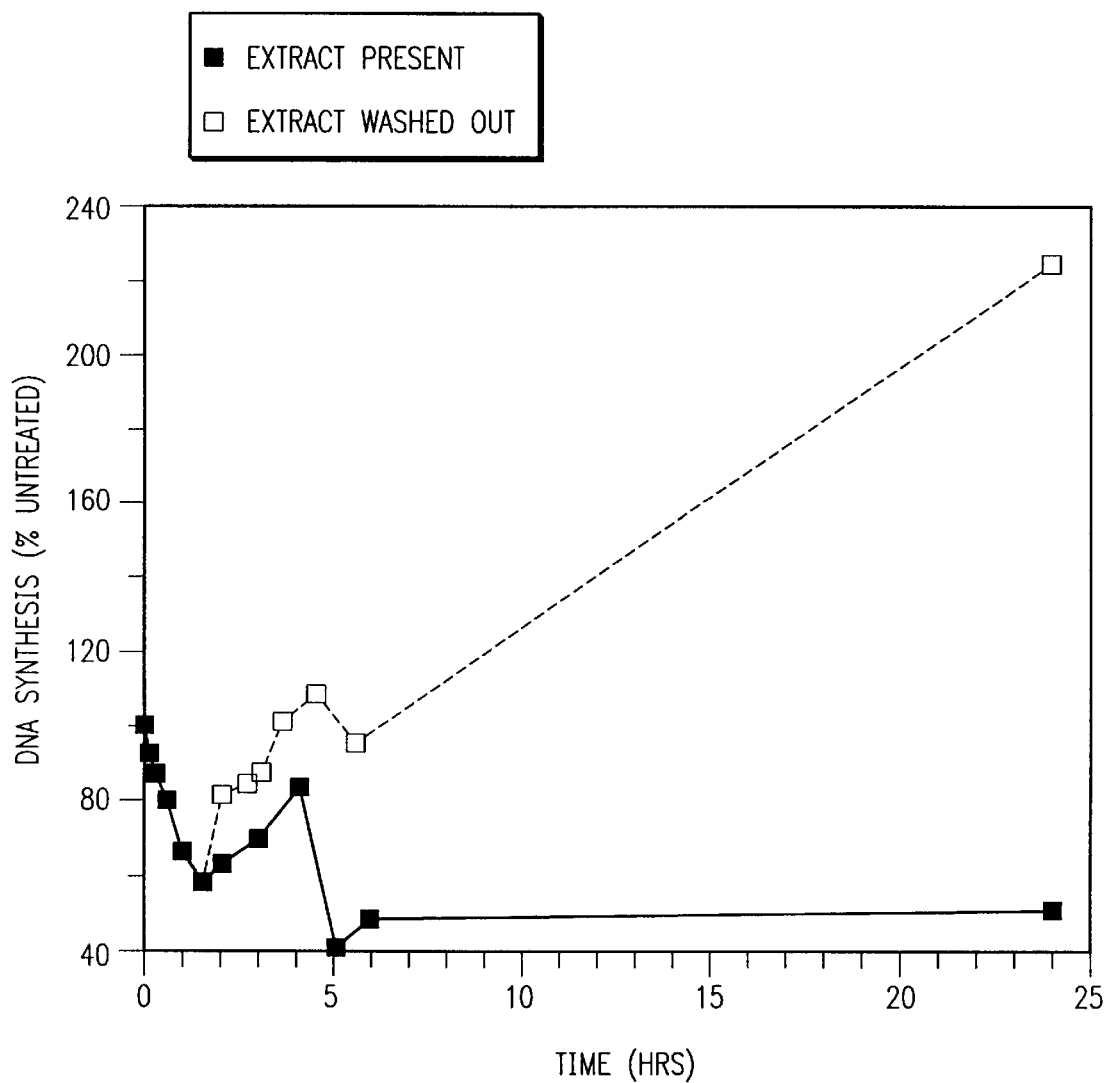

The time-course data also showed that after the removal of SIF extract (by replacing the medium), the cells rapidly resume DNA synthesis (See FIGS. 4 and 5, open circles and squares). Thus, SIF treatment results in the reversible inhibition of DNA synthesis.

Extracts prepared from non-irradiated cells exhibited no detectable SIF activity.

6.2.1. Assay for MIF-Mediated Inhibition of Cell Division in Normal Cells In Vitro Cultures of normal (non-AT) human fibroblasts and hematological cells were grown and labeled essentially as outlined in Section 6.4. MIF extract was then added to the cells for less than two hours. Next, the extent of cell division was monitored by counting the total number of cells using methods well known to those of skill in the art. For example, direct cell counting was performed using a Coulter Counter. The data were normalized relative to control cultures and calculated as a function of the concentration of MIF extract used, or a timecourse of the amount of cell division was tracked over the hours following MIF addition.

6.3. Biochemical Characteristic of SIF and MIF-Factors

At least two distinct factors have been identified to date. These have been designated as $G_1$-arresting factor (SIF factors) and $G_2$-arresting factor(MIF factors). Both have apparent molecular weights greater than 3,500 daltons. Preliminary studies have identified both heat stable ($G_2$-arresting factor) and heat labile ($G_1$-arresting factors) forms of activity which are able to temporarily and reversibly inhibit DNA synthesis in normal cells, and temporarily and reversibly inhibit cell division in normal cells. Both SIF and MIF activities are stable at room temperature for at least 48 hours.

Both SIF and MIF activities bind heparin columns; however, higher salt is required to elute the SIF activity than the MIF activity. These data indicate that at least two distinct activities are present in the irradiated culture extracts.

6.4. Signal Transduction Inhibitor Studies

Human fibroblasts strains GM38, GM43, GM730 (derived from clinically normal donors, and obtained from the NIGMS Human Genetic Mutant Cell Repository, Camden, N.J.), AT2BE (from a patient with AT complementation group A, obtained from the American Type Culture Collection (ATCC), Rockville, Md.), and 1873T and 2674T (from two patients with Li-Fraumeni syndrome, harboring a p53 mutation, were obtained from Meloy Laboratories, Springfield, Va.), were cultivated at 37° C. in Ham's medium supplemented with 10 percent (v/v) fetal bovine serum (FBS), 1 mM glutamine, 100 units penicillin G/ml/ 100 μg streptomycin sulfate/ml (pen/strep) in a humidified atmosphere of 5 percent $CO_2$ in air.

The transformed human cell lines GM3714 (normal), GM2783, VKE (provided by R. A. Gatti, University of California, Los Angeles, Calif.), and the human leukemic cell line HL-60 (obtained from the NIGMS Human Genetic Mutant Cell Repository, Camden, N.J.) were grown in RPMI1640 medium supplemented with 15 percent (v/v) FBS, 1 mM glutamine and pen/strep. All cultures were free of mycoplasma contamination as assayed by the method of Schneider et al., 1974, Exp. Cell. Res. 84:311–318.

Cell cultures were inoculated at about $10^5$ cells/60 mm dish (fibroblasts), or at about $2\times10^5$ cells/ml in 25 ml flasks (hematologic cells) and incubated in growth medium as indicated in Section 6.4. After incubation overnight, the medium was changed to one containing 180 Bq/ml [methyl-$^{14}$C]thymidine (dThd), (stock specific activity $2\times10^9$ Bq/mmol), and incubated for an additional 18–20 hours. After removal of the radioactive medium, cultures were exposed to 0–40 Gy of $^{60}$C γ radiation (Gammacell 220, Atomic Energy of Canada Limited, ON) at a dose rate of about 60 Gy/min. Duplicate samples were used for each set of samples and test conditions. Immediately after irradiation (or sham/control treatment), cultures were incubated in nonradioactive medium for 1 hour, and then pulse labeled with medium containing $5.5\times10^5$ Bq/ml [methyl-$^3$H]dTHd (specific activity, $3\times10^{12}$ Bq/mmol) for 30 min. The corresponding irradiated and control (sham-treated) cells were lysed and the amounts of trichloroacetic acid-precipitable present in the samples were determined (Lehman et al., 1979 Cancer Res. 39:4237–4241). The rate of DNA synthesis was expressed as a percentage of the resulting $^3$H/$^{14}$C ratios for irradiated cultures as compared with the corresponding control cultures (Mirzayans and Paterson, 1991, *Carcinogenesis* 12:19–24).

Various inhibitors of signal transduction were used to assess which signal transduction pathway might be triggered/utilized by SIFs. The inhibitors used included 1 -(5-isoquinolinylsulfonyl)-2-methylpiperazine (H7), N-(6-aminohexyl)-5-chloro-1-naphthalenesulfonamide (W7), N-(4-aminobutyl)-5-chloro-1-napthalenesulfonamide (W13), staurosporine, and 12-O-tetradecanoylphorbol-13-acetate (TPA). One mM stock solutions of H7, W7, and W13 were prepared in distilled water and stored in the dark at 4° C., and staurosporine and TPA were dissolved in DMSO, at 0.1 mM and 1 mg/ml respectively, and stored at −70° C. All chemicals were purchased from Sigma Chemical Co. (St. Louis, Mo.).

Each inhibitor was added to cell cultures at a concentration that did not inhibit DNA synthesis to an extent that it was less then fifty percent that of untreated control cultures. After inhibitor addition, the cells were irradiated and the amount of radioresistant DNA synthesis (RDS) was determined.

6.4.1. Results

Both calmodulin inhibitors (W7 and W13) conferred the RDS phenotype to normal cells. However, inhibitors of Protein Kinase C (H7, staurosporine, and TPA) did not confer an RDS phenotype to normal cells unless relatively high concentrations of H7 (>50 μM) or staurosporine (10 μM) were used. These data indicate that irradiation induced inhibition of DNA synthesis is largely modulated by a calmodulin-dependent pathway, and that AT cells are deficient in this pathway with a PKC-modulated pathway also playing a role. Correspondingly, in being derived from normal cells, the presently claimed SIFs presumably comprise elements from both calmodulin-dependent and PKC-mediated signal transduction pathways which are triggered in response to chromosomal damage.

6.5. Characterization of A $G_1$-Arresting Factor in SIF Extract

Figure 6:
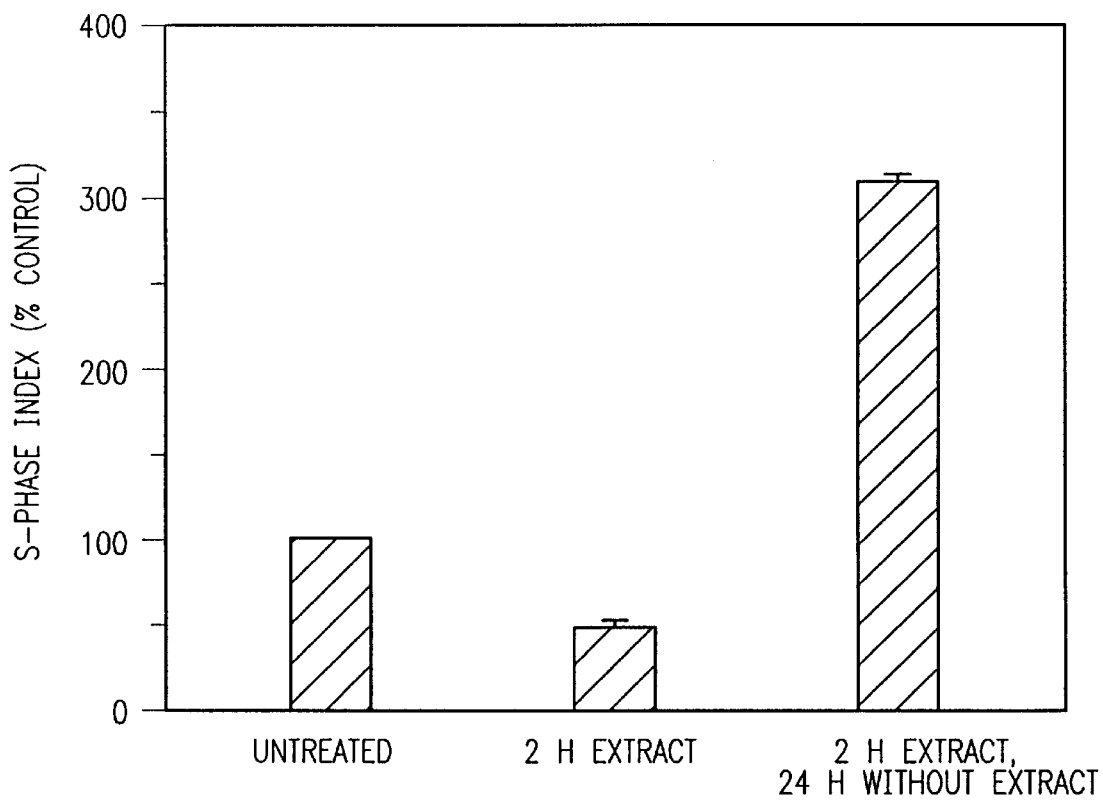
FIG. 6 shows that SIF factor also comprises a $G_1$-arresting activity since two hours after treatment, roughly half as many cells may be found in S-phase as compared to untreated cultures, and after extract is removed, over twice as many cells are in S-phase when compared to untreated cultures.

In order to further characterize the DNA synthesis inhibiting activity of SIF extracts, cells were treated with SIF extract for two hours, after which the fraction of cells in S phase at 0 and 24 hours post extract-exposure was determined by autoradiography (see above). These data are presented in FIG. 6 and show that SIF treatment resulted in a two-fold reduction in cells in S-phase whereas cells that had been treated and subsequently removed from extract for 24 hours had three-fold more cells in S-phase then untreated control cells. These data indicate that SIF extract also comprises a $G_1$-S phase arresting factor and may substantially synchronize cell growth.

6.5.1. Comparison of Effect of $G_1$-Arresting Factor on Normal and Tumor Cells FIG. 8 depicts a chart showing the differential responses of normal human fibroblasts (strain GM38) and human alveolar tumor cells (strain A549) to irradiated HeLa cell extracts. Both strains were treated with extracts for two hours and, as indicated, the rate of DNA synthesis was determined either immediately (0 hr) or following a 24 hour incubation in fresh growth medium. DNA synthesis was measured as in section 6.2.

The Figure demonstrates that immediately after extract treatment, the rates of DNA synthesis in GM38 and A549 cells were reduced to about 60% and about 50% of control, respectively. During the 24 hour post-treatment incubation, the rate of synthesis recovered to control levels in GM38 cells, but dramatically reduced in the tumor cell line, attaining only about 10% of control values. Hence, the reversible inhibition of DNA synthesis following addition of SIFs occurred only in normal cells, and not in tumor cells.

6.6. Damage Recognition Factor Assay

Inhibition of DNA synthesis at early times after irradiation reflects inhibition of both the replicon initiation and chain elongation processes in the cells which have already initiated DNA synthesis (i.e., are in S phase). Thus, any factor that mediates the inhibition of these processes must directly act in the cell nucleus. To determine whether SIF extract also comprises an activity capable of exerting intracellular inhibition of DNA synthesis, normal cells were microinjected with SIF extracts prepared from irradiated and nonirradiated HeLa cells. Cells microinjected with SIF extracts exhibited marked reduction in DNA synthesis as compared cells injected with control extracts/PBS. Thus, SIF extract comprises DNA synthesis inhibiting activities that are able to inhibit DNA synthesis after both external and internal addition. The intracellularly active SIF component is hereby defined as damage recognition factors (DRF). DRF is thought to represent a downstream messenger or effector that is normally produced/triggered by a SIF-receptor initiated calmodulin dependent signal cascade.

6.7. Characterization of A $G_2$-Arresting Factor in MIF Extract

In order to further characterize the mitosis inhibiting activity of MIF extracts, cells were treated with MIF extract for less than two hours. It was found that the cell cycle was arrested in the $G_2$-phase, and thereby inhibited from beginning mitosis. In addition, as shown in FIG. 7c, there was a decrease in the concentration of p21, a protein which inhibits transition from the $G_1$-phase to the S-phase. Hence, the cells that were previously arrested in the $G_1$-phase due to the SIFs, were now released from the $G_1$-checkpoint and entered the S-phase of the cell-cycle. These data indicate that MIF extract also comprises a $G_2$-M phase arresting factor and may substantially synchronize cell growth.

All cell types used above, or contemplated equivalents thereof, are presently available from either commercial sources or the American Type Culture Collection (ATCC), Rockville, Md.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

What is claimed is:

1. A method of making a composition comprising at least about 1 unit/ml to about 16,000 units/ml of DNA synthesis inhibiting factor (SIF) activity or at least about 1 unit/ml mitosis inhibiting factor (MIF), comprising the steps of:
    a) irradiating, with from about one to about six Gy γ rays, a culture of normal, fibroblast cells;
    b) incubating said cells for a period of about 24 hours;
    c) releasing said SIF or MIF from said cells;
    d) centrifuging said culture; and
    e) concentrating the supernatant from step (d).

2. The method of claim 1, wherein said step (e) further comprises chromatographically fractionating said supctnatant.

3. The method of claim 1, wherein said step (c) further comprises lysing said cells.

4. The method of claim 1, wherein said step (e) further comprises passing the supernatant through an AMICON™ ultrafiltration unit.

5. The method of claim 1, wherein said step (e) further comprises precipitation of said supernatant with ammonium sulfate.

6. The method of claim 1, wherein said step (e) further comprises dialyzing said supernatant against phosphate buffered saline (PBS).

7. The method of claim 1, further comprising the step of:
f) passing said supernatant through a heparin column.

8. A method of making a composition comprising at least about 1 unit/ml of MIF activity, comprising the steps of:
a) irradiating, with about 40 Gy γ rays, a culture of human tumor cells;
b) incubating said cells for a period of about 0.5 hours;
c) reasing said MIF from said cells;
d) centrifuging said culture; and
e) concentrating the supernatant from step d.

9. The method of claim 8, wherein said step (e) further comprises chromatographically fractionating said supernatant.

10. The method of claim 8, wherein said step (c) further comprises lysing said cells.

11. The method of claim 8, wherein said step (e) further comprises passing the supernatant through an AMICON™ ultrafiltration unit.

12. The method of claim 8, wherein said step (e) further comprises precipitation of said supernatant with ammonium sulfate.

13. The method of claim 8, wherein said step (e) further comprises dialyzing said supernatant against PBS.

14. The method of claim 8, further comprising the step of:
f) passing said supernatant through a hepatin column.

15. A composition made by the method of claim 1.

16. The composition of claim 15, wherein said composition comprises at least about 1 unit/ml of SIF activity up to about 16,000 units/ml.

17. The composition of claim 16, wherein said SIF activity is heat labile.

18. The composition of claim 16, wherein said SIF activity is not inactivated by boiling for about 10 minutes.

19. The composition of claim 16, wherein said SIF activity is stable at room temperature for at least 48 hours.

20. The composition of claim 16, wherein the SIF activity binds to a heparin column.

21. A composition made by the method of claim 1 or 8.

22. The composition of claim 21, wherein said composition comprises at least about 1 unit/ml of MIF activity.

23. The composition of claim 22, wherein said MIF activity is not inactivated by boiling for about 10 minutes.

24. The composition of claim 22, wherein said MIF activity is stable at room temperature for at least 48 hours.

25. The composition of claim 22, wherein said MIF activity binds to a heparin column.

26. A method of inhibiting DNA synthesis in a mammalian cell, comprising:
extracellularly administering the composition of claim 16 to a mammalian cell in all amount sufficient to inhibit DNA synthesis.

27. The method of claim 25, wherein said composition is administered in a therapeutically effective amount to an individual suffering from a proliferative disorder.

28. The method of claim 25, wherein said method produces a population of cells substantially synchronized in their growth.

29. A method of inhibiting mitosis in a mammalian cell, comprising:
administering the composition of claim 22 to a mammalian cell in an amount sufficient to inhibit mitosis.

30. The method of claim 29, wherein said composition is administered in a therapeutically effective amount to an individual suffering from a proliferative disorder.

31. The method of claim 29, wherein said method produces a population of cells substantially synchronized in their growth.

32. The method of claim 27, wherein said proliferative disorder is cancer.

33. The method of claim 30, wherein said proliferative disorder is cancer.

34. The method of claim 1, wherein said step (c) further comprises sonicating said cells.

35. The method of claim 8, wherein said step (c) further comprises sonicating said cells.

* * * * *